US008168833B2

(12) United States Patent
Zhao et al.

(10) Patent No.: US 8,168,833 B2
(45) Date of Patent: May 1, 2012

(54) SCHWARTZ REAGENTS: METHODS OF IN SITU GENERATION AND USE

(75) Inventors: Yigang Zhao, Kingston (CA); Victor A. Snieckus, Kingston (CA)

(73) Assignee: Queen's University at Kingston, Kingston, Ontario (CA)

( * ) Notice: Subject to any disclaimer, the term of this patent is extended or adjusted under 35 U.S.C. 154(b) by 237 days.

(21) Appl. No.: 12/630,185

(22) Filed: Dec. 3, 2009

(65) Prior Publication Data

US 2010/0145060 A1    Jun. 10, 2010

Related U.S. Application Data

(60) Provisional application No. 61/119,916, filed on Dec. 4, 2008.

(51) Int. Cl.
| | |
|---|---|
| C07C 45/90 | (2006.01) |
| C07C 37/04 | (2006.01) |
| C07C 233/00 | (2006.01) |
| C07D 311/00 | (2006.01) |
| C07D 401/00 | (2006.01) |
| C07D 209/04 | (2006.01) |
| C07F 9/02 | (2006.01) |
| C07F 7/04 | (2006.01) |

(52) U.S. Cl. .......... 568/436; 568/13; 568/449; 568/730; 549/214; 546/278.1; 564/184; 548/469; 556/436

(58) Field of Classification Search .................. 568/436, 568/449, 738; 549/214; 546/278.1
See application file for complete search history.

(56) References Cited

U.S. PATENT DOCUMENTS

| | | | | |
|---|---|---|---|---|
| 5,399,689 A | * | 3/1995 | Buchecker et al. | ........... 544/296 |
| 5,679,807 A | | 10/1997 | Murray et al. | |
| 2007/0060561 A1 | * | 3/2007 | Corey et al. | .............. 514/210.05 |

OTHER PUBLICATIONS

Shindo et al. A Catalytic Method for Asymmetric Nucleophilic Aromatic Substitution Giving Binaphthyls. Journal of the American Chemical Society, (1992), vol. 114, 8732-8733.*
Buchwald, S.L., "Schwartz's reagent", Organic Synthesis. Coll. vol. 9 p. 162 (1998): Vo. 71: p. 77-82 (1993).
Dang, L, et al., "DFT studies on the borylation of . . . enolates of Cu, B, and Si", Organometallics 27: 4443-4454 (2008).
Endo, J., et al., "Theoretical study on hydrozirconation", Organometallics 12: 2777-2787 (1993).
Ganem, B., et al., "Paclitaxel from primary taxanes: A perspective on creative invention in organozirconium chemistry", J. Org. Chem. 72(11): 3981-3987 (2007).
Huang, Z., et al., "A convenient and geniune equivalent to HZrCp2Cl generated in situ from ZrCp2Cl2-DIBAL-H", Org. Lett. 8(17): 3675-3678 (2006).
Lipshutz, B.H., et al., "A new method for the in situ generation of Cp2Zr(H) Cl", Tetrahedron Lett. 31(50): 7257-7260 (1990).
Makabe, H., et al., "Hydrogen transfer hydrozirconation of alkenes with . . . and Pd", Eur. J. Org. Chem.: 969-971 (1999).
Nienkemper, K., et al., "Synthesis of double-end-capped polyethylene by a . . . benzyl complex", Organometallics 27: 5867-5875 (2008).
Pankratyev, E.Y., et al., "DFT study on mechanism of olefin . . . with Cp2ZrCl2", Organometallics 28: 968-977 (2009).
Schedler, D.J.A., et al., "Reduction of secondary carboxamides to imines", J. Org. Chem. 61: 4115-4119 (1996).
Schedler, D.J.A., et al., "Reductive deoxygenation by Cp2ZrHCl: Selective formation . . . of amides", Tetrahedron Lett. 34(32): 5035-5038 (1993).
Spletstoser, J.T., et al., "One-step facile synthesis of deuterium labeled . . . using Cp2Zr(D)Cl", Tetrahedron Lett. 45: 2787-2789 (2004).
Spletstoser, J.T., et al., "Mild and selective hydrozirconation of . . . insight", J. Am. Chem. Soc. 129: 3408-3419 (2007).
Stephens, P.J., et al., "Ab Initio calculation of vibrational absorption and circular . . . force fields", Phys.Chem, 98(45): 11623-11627 (1994).
Ugolotti, J., et al., "Five-membered zirconacycloallenoids: Synthesis and . . . allenoid compounds", J. Am. Chem. Soc. 131: 1996-2007 (2009).
Wadt, W.R., et al., "Ab initio effective core potentials for molecular . . . Na to Bi", J. Chem. Phys. 82(1): 284-298 (1985).
Wailes, P.C., et al., "Hydrido complexes of zirconium I. preparation", J. Organomet. Chem. 24: 405-411 (1970).
Wang, J., et al., "DFT study on the mechanism of amides to aldehydes using Cp2Zr(H)Cl", Organometallics 29: 42-51 (2010).
White, J.M., et al., "A novel and expeditious reduction of tertiary . . . using Cp2Zr(H)Cl", J. Am. Chem. Soc. 122: 11995-11996 (2000).
White, J.M., et al., "Selective reduction with Cp2ZrHCl", Chemical Innovation 30(12): 17-21 (2000).
Wipf, P., et al., "Synthetic applications of organochlorozirconocene complexes", Tetrahedron 52(40): 12853-12910 (1996).
Wipf, P., et al., "Hydrozirconation and its applications", Topics in Organometallic Chemistry 8:1-25 (2005).

* cited by examiner

*Primary Examiner* — Sikarl Witherspoon
(74) *Attorney, Agent, or Firm* — Angela Lyon; Carol Miemicki Steeg; Emma Saffman

(57) ABSTRACT

Embodiments of the invention provide a method of using Schwartz Reagent, $Cp_2Zr(H)Cl$, without accumulating or isolating it. Methods provide mixtures of $Cp_2ZrCl_2$, reductants that selectively reduce $Cp_2ZrCl_2$, and substrates. After reaction of $Cp_2ZrCl_2$ and the reductant, an intermediate reduction product is formed, apparently Schwartz Reagent. The in situ Schwartz Reagent then selectively reduces certain functional groups on the substrate. Substrates include tertiary amides, tertiary benzamides, aryl O-carbamates, and heteroaryl N-carbamates, which are reduced to aldehydes, benzaldehydes, aromatic alcohols, and heteroaromatics, respectively. Compared to prior methods, reagents are inexpensive and stable, reaction times are short, and reaction temperature in certain cases is conveniently room temperature. It has been estimated that using the in situ method described herein instead of synthesized or commercially obtained Schwartz Reagent provides a 50% reduction in cost.

43 Claims, 2 Drawing Sheets

CGS-25019C
a leukotriene B4 (LTB4) antagonist which has antirheumatic,
anti-inflammatory and antipsoriatic activities BW373U88
a non-peptidic, systemically-active δ opioid agonist ascochlorin-6 (AS-6)
a hypoglycemic agent for treatment of diabetes TAN-931
a nonsteroidal aromatase inhibitor PD-116152
a phenazine antitumor antibiotic

SCHWARTZ REAGENTS: METHODS OF IN SITU GENERATION AND USE

RELATED APPLICATION

This application claims the benefit of the filing date of U.S. Provisional Patent Application No. 61/119,916, filed on Dec. 4, 2008, the contents of which are incorporated herein by reference in their entirety.

FIELD OF THE INVENTION

The field of the invention is chemical reduction reactions, particularly, selective reduction of certain functional groups using Schwartz Reagent, a reductant that specifically targets certain functional groups.

BACKGROUND OF THE INVENTION

A reductant known as Schwartz Reagent ($Cp_2Zr(H)Cl$ or bis(cyclopentadienyl) zirconium(IV) chloride hydride) is known in synthetic organic chemistry. Examples of conversion reactions where the Schwartz Reagent is commonly used include adding HZr (hydrozirconation reactions), converting a compound with a secondary amide moiety to a compound with an imine moiety, and converting a compound with a tertiary amide moiety to a compound with an aldehyde moiety. (For hydrozirconation see: Wipf, P., Kendall, C., *Topics in Organometallic Chemistry* 2005, 8, 1-25; Marek, I., *Titanium and Zirconium in Organic Synthesis*; Wiley-VCH: Weinheim, 2002; Wipf, P., Jahn, H., *Tetrahedron* 1996, 52, 12853-12910. For sec-amide to imine see: Schedler, D. J. A., Li, J., Ganem, B. *J. Org. Chem.* 1996, 61, 4115-4119; Schedler, D. J. A., Godfrey, A. G., Ganem, B. *Tetrahedron Lett.* 1993, 34, 5035-5038. For tert-amide to aldehyde see: White, J. M., Tunoori, A. R., Georg, G. I., *J. Am. Chem. Soc.* 2000, 122, 11995-11996; White, J. M., Tunoori, A. R., Georg, G. I., *Chemical Innovation* 2000, 30, 23.28; Huang, Z., Negishi, E.-I., *Org. Lett* 2006, 8, 3675-3678; and Spletstoser, J. T., White, J. M., Georg, G. I., *Tetrahedron Lett.* 2004, 45, 2787-2789.)

SUMMARY OF THE INVENTION

A first aspect of the invention provides a method of converting a substrate to a product comprising combining at substantially the same time selected amounts of A, B, and D in a solvent; allowing time for reactions to proceed; and obtaining product E; where A is $Cp_2ZrCl_2$, B is a reducing agent that preferentially reacts with A to form an intermediate, D is a substrate that is reduced by the intermediate, and E is a reduced form of D.

In certain embodiments of the first aspect, D is a tertiary amide and E is an aldehyde. The time allowed for reactions to proceed may be greater than about two minutes. In some embodiments the time allowed for reactions to proceed is about two to about ten minutes. In some embodiments, tertiary amide is an aryl tertiary amide. In some embodiments, aryl is heteroaryl. In some embodiments, tertiary amide is an aliphatic tertiary amide.

In other embodiments of the first aspect, D is an aryl O-carbamate and E is an aromatic alcohol. In still other embodiments of the first aspect, D is an aromatic N-heteroaryl N-carbamate and E is an N-heteroaryl compound.

In some embodiments of the invention, B is $LiAlH(OBu-t)_3$, $LiBH(s-Bu)_3$, or a combination thereof.

In certain embodiments of the first aspect, the combination is at about room temperature. In other embodiments, the combination starts at about 0° C. and is allowed to warm to about room temperature. In certain embodiments of the first aspect, the solvent comprises THF, DME, dioxane, 2-MeTHF, diethyl ether, $CH_2Cl_2$, $CHCl_3$, toluene, or a combination thereof.

In some embodiments of the first aspect, the selected amounts of A, B, and D are an excess of A and B over D. Ratios of A and B over tertiary amides include 1.4:1.4:1; 1.5:1.5:1; 1.8:1.8:1; and 2:2:1. Ratios of A and B over O-carbamates or N-carbamates include 3:3:1.

A second aspect of the invention provides a kit for reducing a substrate comprising A and B, where A is $Cp_2ZrCl_2$ and B is a reducing agent that selectively reduces A. B may be $LiAlH(OBu-t)_3$, $LiBH(s-Bu)_3$, or a combination thereof. Kits may further comprise instructions for use of A and B with substrate. Such instructions may comprise one or more of text or schematics or both printed on paper or other material; text or schematics or both saved on electronic-readable medium such as a floppy disc, CD-ROM, DVD-ROM, Zip disc, videotape, or audio tape; direction to an Internet web site; or mail including electronic mail.

Kits may further comprise solvent. Such solvent may be THF, DME, dioxane, 2-MeTHF, diethyl ether, $CH_2Cl_2$, $CHCl_3$, toluene, or a combination thereof.

A third aspect of the invention provides a compound E made by the methods of the first aspect.

In some embodiments of the first aspect, D is a substrate of Table 1 and E is a corresponding product of Table 1. In some embodiments of the first aspect, D is a substrate of Table 2 and E is a corresponding product of Table 2. In some embodiments of the first aspect, D is a substrate of Table 3 and E is a corresponding product of Table 3. In some embodiments of the first aspect, D is a substrate of Table 4 and E is a corresponding in situ method product of Table 4. In some embodiments of the first aspect, D is a substrate of Table 7 and E is a corresponding product of Table 7. In some embodiments of the first aspect, D is a substrate of Table 8 and E is a corresponding product of Table 8. In some embodiments of the first aspect, wherein the time allowed for reactions to proceed is greater than about two minutes.

In some embodiments of the first aspect, E is a hydrozirconation product of D. In some embodiments of the first aspect, E is further reacted to form a new product. In some embodiments of the first aspect, E is further reacted with $X_2$ where X is a halide. In some embodiments of the first aspect, E is further reacted with $ZnX_2$ where X is a halide.

Other objects and advantages of the present invention will become apparent from the disclosure herein.

BRIEF DESCRIPTION OF THE DRAWINGS

For a better understanding of the invention and to show more clearly how it may be carried into effect, reference will now be made by way of example to the accompanying drawings, which illustrate aspects and features according to embodiments of the present invention, and in which.

DETAILED DESCRIPTION OF THE INVENTION

Definitions

Figure 1:
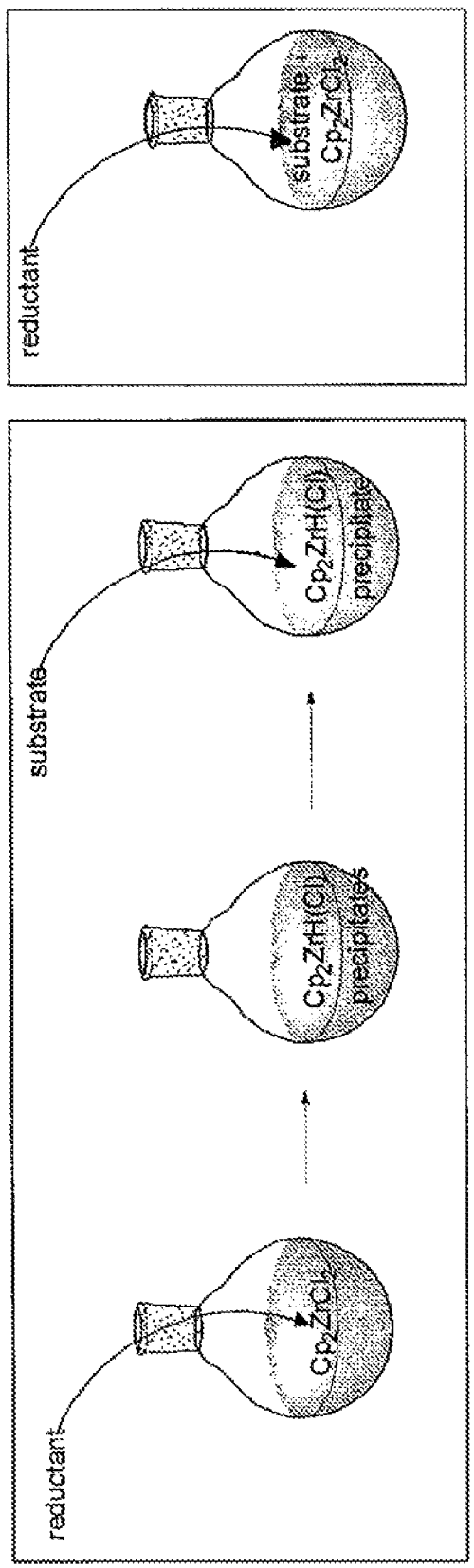
FIG. 1 depicts two schematics that compare the previous one vessel, two-step method of preparing, accumulating, and then using Schwartz Reagent to reduce a substrate, with the current in situ method of preparing and using Schwartz Reagent (without accumulating it) to reduce a substrate.
Figure 2:
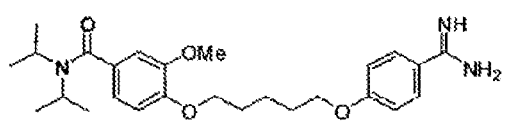
FIG. 2 depicts chemical structures of five compounds whose synthesis can be simplified by the present in situ method.
Figure 2:
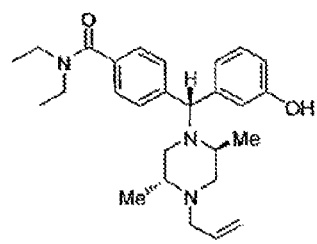
Figure 2:
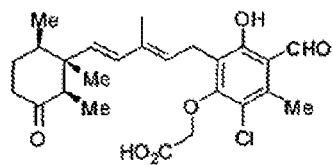
Figure 2:
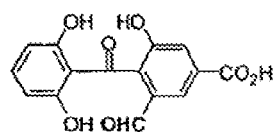
Figure 2:
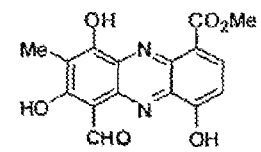

As used herein, the term "aliphatic" refers to hydrocarbon moieties that are straight chain, branched or cyclic, may be alkyl, alkenyl or alkynyl, and may be substituted or unsubstituted.

As used herein, the terms "short chain aliphatic" or "lower aliphatic" refer to $C_1$ to $C_4$ aliphatic; the terms "long chain aliphatic" or "higher aliphatic" refer to $C_5$ to $C_{25}$ aliphatic.

As used herein, "heteroatom" refers to non-hydrogen and non-carbon atoms, such as, for example, O, S, and N.

As used herein, "Boc" refers to tert-butoxycarbonyl. As used herein, "Cbz" refers to benzyloxycarbonyl. As used herein, "TMS" refers to trimethylsilyl. As used herein, "Tf" refers to trifluoromethanesulfonyl.

As used herein, the term "aryl" means aromatic, including heteroaromatic.

As used herein, the term "amide" means a moiety including a nitrogen where at least one of the groups bound to the nitrogen is an acyl (i.e., C(=O)—) group.

As used herein, the term "reduction" or "reduce" refers to a reaction that converts a functional group from a higher oxidation level to a lower oxidation level. Typically, a reduction reaction either adds hydrogen or removes an electronegative element (e.g., oxygen, nitrogen, or halogen) from a molecule. Oxidation level refers to the number of bonds between a carbon atom and heteroatoms. For clarity, three reduction examples will now be described. First, in a substrate that has a —C—C(=O)—NR$_2$ amide moiety, there are three bonds between C and heteroatoms, so the oxidation level of C is three. When the substrate is reduced, the amide moiety is converted to a product that has a —C—C(=O)—H aldehyde moiety. Since there are two bonds between C and a heteroatom in the aldehyde moiety, the oxidation level of C in the product is two. Thus a reduction has occurred, resulting in a change in the oxidation level of C from three in the substrate to two in the product. Second, in a substrate that has a —C—O—C(=O)—NR$_2$ O-carbamate moiety, there are four bonds between C and heteroatoms, so the oxidation level of C is four. When the substrate is reductively cleaved, it forms two products, an alcoholic product and the amide H—C(=O)—NR$_2$. Since there are three bonds between C and heteroatoms in the amide product, the oxidation level of C is three. Thus a reduction has occurred, resulting in a change in the oxidation level of C from four in the substrate to three in the amide product. Third, in a substrate that has a >N—C(=O)—NR$_2$ N-carbamate moiety (where >mean two bonds), there are four bonds between C and heteroatoms, so the oxidation level of C is four. When the N-carbamate moiety is reductively cleaved, it forms two products, a product that has a >N—H moiety and the amide H—C(=O)—NR$_2$ are formed. Since there are three bonds between C and heteroatoms in the amide product, the oxidation level of C is three. Thus a reduction has occurred, resulting in a change in the oxidation level of C from four in the substrate to three in the amide product.

As used herein, the term "benzamide" refers to a compound with a phenyl aryl group that has a —C(=O)NR$^b$R$^c$ group bound to one of its ring atoms, where R$^b$ and/or R$^c$ may be hydrogen, substituted or unsubstituted lower aliphatic, and higher aliphatic.

As used herein, the term "Georg method" refers to a method of using pre-prepared Schwartz Reagent as a reducing agent that specifically targets certain functional groups, as described in White, J. M., Tunoori, A. R., Georg, G. I., *J. Am. Chem. Soc.* 2000, 122, 11995-11996.

As used herein, the term "tertiary amide" means a moiety including a nitrogen that is bonded to a carbonyl group where the nitrogen is also bonded to non-hydrogen moieties, i.e., R$^a$C(=O)NR$^d$R$^e$ where R$^d$ and/or R$^e$ are typically aliphatic, but are not hydrogen. This should not be confused with a lesser-known use of the term "tertiary amide"; specifically, where there are three acyl groups on an amide nitrogen, i.e., [R$^a$C(=O)]$_3$N (this latter use is discussed in IUPAC Compendium of Chemical Terminology, 2$^{nd}$ ed. (1997) by Alan D. McNaught and Andrew Wilkinson, Royal Society of Chemistry, Cambridge, UK).

As used herein, "aliphatic tertiary amide" refers to a tertiary amide (i.e., R$^a$C(=O)NR$^d$R$^e$) where R$^a$, R$^d$ and R$^e$ are not aryl, but may have aryl substituents. In some aliphatic tertiary amide embodiments described herein, the atom of R$^a$ that is attached to the acyl carbon is a saturated carbon.

As used herein, "aryl tertiary amide" refers to a tertiary amide (i.e., R$^a$C(=O)NR$^d$R$^e$) where the atom of R$^a$ that is attached to the acyl carbon is an aryl moiety, which includes a heteroaryl moiety.

As used herein, the term "aryl O-carbamates" refers to an compound wherein at least one aryl ring has a —OC(=O)NR$_2$ moiety bound to one of its ring atoms.

As used herein, the term "LiAlH(OBu-t)$_3$" means lithium tri-(tert-butoxy)aluminum hydride.

As used herein, the term "LiBH(s-Bu)$_3$" means lithium tri-(sec-butyl)borohydride.

As used herein, the term "LiAlH$_4$" means lithium aluminum hydride.

As used herein, the term "DIBAL-H" means diisobutylaluminum hydride.

As used herein, the term "Schwartz Reagent" means bis(cyclopentadienyl)-zirconium(IV) chloride hydride, which is also referred to herein as Cp$_2$Zr(H)Cl.

As used herein, "A" or Schwartz Reagent Precursor means bis(cyclopentadienyl)-zirconium(IV) dichloride, which is also referred to herein as Cp$_2$ZrCl$_2$.

As used herein, "B" means reductants that selectively reduce A. Non-limiting examples of B include LiAlH(OBu-t)$_3$, LiBH(s-Bu)$_3$, and combinations thereof.

As used herein, "D" means a substrate that is desired to be selectively reduced. Non-limiting examples of D include tertiary amides, O-carbamates, and aryl N-carbamates.

As used herein, "E" means a desired product. Non-limiting examples of E include an aldehyde when D is a tertiary amide, and a phenolic compound when D is an aryl O-carbamate.

As used herein, the term "in situ" has its ordinary chemical meaning of presence of a molecule in a reaction where it is generated therein instead of separately added.

As used herein, the term "substrate" means a compound that is desired to be converted to a product compound. In the context of this description, "substrate" is used, for example, to mean a tertiary amide that one desires to have reduced to its corresponding aldehyde. Another example of a substrate in the context of this description is an aryl O-carbamate that one desires to have reduced to the corresponding phenol. Yet another example of a substrate in the context of this description is a N-heteroaryl N-carbamate that one desires to reduce to the corresponding aromatic N-heterocycle. The terms "substrate" and "D" are used interchangeably herein.

As used herein, the solvent DME is 1,2-dimethoxylethane.

As used herein, the solvent THF is tetrahydrofuran.

General Discussion of Schwartz Reagent

Reduction of amides to aldehydes using the Schwartz Reagent is a relatively recent discovery (White et al. 2000).

Direct amide to aldehyde reduction is an important transformation. While benzamides are recalcitrant to conversion, especially by hydrolysis to benzoic acids, benzaldehydes are readily converted to other functional groups (e.g., acids, esters, nitriles, hydrazones, oximes) and are widely used in modern synthetic reactions for the preparation of other useful derivatives for organic synthesis, e.g., Wittig reaction, aldol condensation, and cyanohydrin formation. The significant value of this discovery has been demonstrated, for example, by use of stoichiometric amounts of the Schwartz Reagent in the reduction of secondary amide to imine in a large-scale synthesis of a taxol derivative (see Ganem, B., Franke, R. R. *J. Org. Chem.* 2007, 72, 3981-3987; and Murray, C. K., Zheng, Q. Y., Cheng, X., Peterson, S. K., U.S. Pat. No. 5,679, 807, 1997).

The Schwartz Reagent is a desirable reducing agent because of its specificity for certain functional groups. That is, fewer side reactions occur when the Schwartz Reagent is used when compared to other reducing agents. Accordingly, yields are much higher compared to other conversion methods. For these reasons, the Schwartz Reagent is a useful reducing agent even though it has certain disadvantages including poor solubility, instability (tends to degrade) in the presence of air, light and/or moisture and a tendency to effect over-reduction.

The Schwartz Reagent, $Cp_2Zr(H)Cl$, is commercially available although it is expensive relative to its precursor, $Cp_2ZrCl_2$. Due to the Schwartz Reagent's instability except under inert conditions and its relative expense, many users prepare their own Schwartz Reagent in a first reaction that is distinct from subsequent reactions in which the Schwartz Reagent is used as a specific reducing agent. This two-step method will be described in the next section.

Previous Two-Step Method Including Preparation then Use of Schwartz Reagent

In previous methods of using Schwartz Reagent, it was prepared, accumulated, and isolated by reacting $Cp_2ZrCl_2$ with a reductant, prior to its being used in a separate reaction with a substrate. Thus, in previous methods, during synthesis of Schwartz Reagent, no substrate was present when the Schwartz Reagent Precursor was reduced. When no substrate is present and the only compound present for reduction is Schwartz Reagent Precursor, a variety of reductants can be used, including $LiAlH(OBu-t)_3$, $LiAlH_4$, and sodium bis(2-methoxyethoxy)aluminum hydride ("Red-Al"). Descriptions of syntheses of Schwartz Reagent include a reaction of LiAlH $(OBu-t)_3$ and $Cp_2ZrCl_2$ at room temperature (RT) for about 1 h (see Wailes, P. C., Weigold, H. *J. Organomet. Chem.* 1970, 24, 405-411), a reaction of Red-Al and $Cp_2ZrCl_2$ where reaction time and temperature were not specified (see Carr, D. B., Schwartz, J. *J. Am. Chem. Soc.* 1979, 101, 3521-3531), and a reaction of $LiAlH_4$ and $Cp_2ZrCl_2$ at RT for about 2 h (see Buchwald, S. L., LaMaire, S. J., Nielsen, R. B., Watson, B. T., King, S. M. *Org. Synth.* 1993, 71, 77-82). Such reactions that produce Schwartz Reagent also produce as a byproduct over-reduction product $Cp_2ZrH_2$.

Once prepared, the Schwartz Reagent is readily isolable from the reaction solution, because it precipitates due to its poor solubility in most solvents. However, because it degrades in the presence of air, light and/or moisture, accurately determining the amount of actual Schwartz Reagent obtained in the crude product can be challenging. The crude product is typically contaminated by $Cp_2ZrH_2$, other salts, and degradation products, and it is typically used in its unpurified state to avoid further degradation. The presence of contaminants may decrease the efficiency of the Schwartz Reagent.

Once freshly prepared Schwartz Reagent has been isolated, it is ready for use as a specific reducing agent as described by Georg (White, J. M., Tunoori, A. R., Georg, G. I., *J. Am. Chem. Soc.* 2000, 122, 11995-11996). Reaction conditions for use of the Schwartz Reagent as specific reductant of various aromatic and non-aromatic tertiary amides (again, see White, 2000) were about 15 minutes (min.) to about 30 min. at RT. Yields ranged from 74 to 99%. Due to its poor solubility, it was difficult to determine an appropriate amount of Schwartz Reagent to use. It was common in the two-step method to use an excess of Schwartz Reagent compared to the amount of substrate (i.e., 1.5 to 2 equivalents (eq.) of Schwartz Reagent relative to substrate).

Previous One Vessel, Two-Step Generation of Schwartz Reagent

Due to the Schwartz Reagent's expense and its degradation problem with long-term storage, methods of in situ generation of Schwartz Reagent have been a research target. To date, generation procedures have been studied wherein a single reaction vessel is used but the method remains as two steps. These procedures use hydride sources such as t-BuMgCl (see Makabe, H., Negishi, E., *Eur. J. Org. Chem.* 1999, 969-971), $LiEt_3BH$ (Lipshutz, B. H., Keil, R., Ellsworth, E. L., *Tetrahedron Lett.* 1990, 31, 7257-60), and DIBAL-H (Huang, Z., Negishi, E., *Org. Lett.* 2006, 8, 3675-3678) to produce Schwartz Reagent. A schematic of this one vessel, two-step procedure is depicted in the left box of FIG. 1, which is labelled "Previous Method". As depicted, studies by these authors were based on initial preparation of the Schwartz Reagent followed by addition of a substrate. In such reactions, if the reductant used to generate Schwartz Reagent were to remain, byproducts would contaminate the end product since the reductant would react with the substrate. Thus, the disadvantages of pre-preparation of the Schwartz Reagent would remain in such one vessel, two-step procedures. As discussed above, these disadvantages include over-reduction, poor solubility, and contaminants that may affect efficiency.

Thus there exists a need for a method that combines generating and using Schwartz Reagent in an in situ method so that Schwartz Reagent quickly reacts once generated.

DESCRIPTION OF EMBODIMENTS

In the Georg method, Schwartz Reagent is used as a reductant because it selectively reduces a substrate at certain functional groups. The Georg method uses Schwartz Reagent that has been separately obtained. Although Schwartz Reagent can be purchased, due to its high cost relative to its precursor and its tendency to degrade, many users choose to synthesize it. Accordingly, use of the Schwartz Reagent to obtain a desired product previously meant two separate syntheses. First, Schwartz Reagent was prepared by reacting Schwartz Reagent Precursor and a reductant. Second, the desired product was prepared by reacting Schwartz Reagent with the substrate. The reason for keeping these two reactions separate was to avoid side reactions occurring between the substrate and the reductant. Such side reactions decreased yields of the desired compound in the crude product, and increased the need for purification of the crude product. For these reasons, prior to the instant invention, it was not contemplated to combine Schwartz Reagent Precursor, reductant, and substrate.

In contrast, aspects of the present invention provide a method where Schwartz Reagent can be produced in the presence of the substrate (with which it will react) with substantially no side reactions occurring. Surprisingly, it was discovered that when Schwartz Reagent Precursor is reacted with particular reductants that are selective for Schwartz Reagent Precursor, the substrate does not react with such reductants, and does not react until Schwartz Reagent appears. Thus all three compounds can be combined with substantially no side reactions occurring, so selective reductions using Schwartz Reagent can now be performed in a single step. It has been estimated that using the in situ method described herein instead of synthesized or commercially obtained Schwartz Reagent provides a 50% reduction in cost.

Thus, aspects of the invention provide methods that eliminate the need for advance preparation and isolation of Schwartz Reagent, which is unstable as described previously. In contrast to the Georg method of, first, providing Schwartz Reagent and, second, mixing it with a substrate, aspects of the invention provide advantages of the Georg method but have eliminated disadvantages. Aspects of the invention provide simple and efficient methods using inexpensive reagents that are stable to long term storage. Such methods produce desired product from a single reaction mixture. Thus, this in situ method eliminates the extra step of separately preparing Schwartz Reagent and avoids the problem of over-reduction to $Cp_2ZrH_2$.

Aspects of the invention provide methods of performing selective reductions of substrates without the necessity of pre-preparing Schwartz Reagent. The previously described two-step method can now be replaced by a one-step method wherein three compounds are mixed. In general terms, two of the mixed compounds do not react with the third, instead they selectively react with each other. Their reaction leads to formation of an intermediate reaction product that is only briefly present in the mixture. The reason for the briefness of its presence is that it is selectively reactive toward the third compound in the mixture. Upon reaction of the intermediate reaction product with this third compound, a desired end product is formed.

Thus details of the aspects of the invention will now be described wherein three compounds, A, B and D are all provided in a mixture. A and B react to form an intermediate product, which then reacts with substrate D. A desired product is formed from the reaction of the intermediate product and D. The product is a reduced form of D and is known herein as E. To assist with completeness and speed of reaction, a solvent is also present to solubilize the mixture.

A is Schwartz Reagent Precursor, $Cp_2ZrCl_2$, which is significantly less expensive to purchase than Schwartz Reagent.

B is a reducing agent that is selective for A. In certain embodiments of the invention, B is $LiAlH(OBu-t)_3$, $LiBH(s-Bu)_3$, or a combination thereof. These reducing agents are inert to many functional groups and are selective for others. In the studies performed and described herein, these A-selective reductants did not undergo substantially any side reactions with D when D was tertiary amide, tertiary benzamide, aryl O-carbamate, or heteroaryl N-carabamate. Nor did the reductants undergo reactions with any intermediates formed during these reactions.

As noted above, D is substrate. Examples of D include tertiary amides, tertiary benzamides, aryl O-carbamates, N-carbamates, and aryl N-carbamates including heteroaryl N-carbamates.

As noted above, E is the reaction product of the reduction of substrate, D. Examples of E include aldehydes, benzaldehydes, aromatic alcohols (commonly referred to as phenols), and N-heteroaromatic compounds.

As described above, when Schwartz Reagent Precursor was selectively reduced, an intermediate reaction product formed. Without wishing to be bound by theory, the inventors suggest that the intermediate was Schwartz Reagent, $Cp_2Zr$(H)Cl. In support of the intermediate being Schwartz Reagent, it is noted that the reaction product, which was isolated as a solid, of the reaction of Schwartz Reagent Precursor with $LiAlH(OBu-t)_3$ in THF at RT was indeed Schwartz Reagent (see Wailes, P. C., Weigold, H. *J. Organomet. Chem.* 1970, 24, 405-411). In investigations done to date, the intermediate has shown the same selectivity for certain functional groups as Schwartz Reagent. Therefore, for clarity and convenience, the intermediate of the in situ method is referred to herein as Schwartz Reagent or in situ Schwartz Reagent.

However, the inventors consider it possible that the intermediate is a compound other than Schwartz Reagent. For example, the intermediate could be a more reactive reagent which would explain why it effects reduction of amides very quickly. Comparative studies of reductive cleavage using the Georg method and the present in situ method were conducted for certain compounds. Results of these studies are presented in Table 4. It was determined that shorter reaction times and higher yields were obtained using the in situ method when compared to the Georg method. Notably, at entry 2 of Table 4, the reaction time for the same substrate using the Georg method was 20 min. (72% yield) and using the in situ method was 2 min. (91%).

Upon its formation and generally without precipitating from solvent, the in situ Schwartz Reagent selectively reduced particular functional groups of D and formed the desired product, E. Specifically, in certain embodiments, it selectively reduced functional groups such as tertiary amides to form aldehydes; aryl O-carbamates to form aromatic alcohols; and N-heteroaryl N-carbamates to form N-heteroaryl compounds.

In embodiments of the invention, the Schwartz Reagent was formed in situ and reacted in situ. During most of the reactions described herein, the intermediate did not precipitate from the reaction mixture. It underwent reaction soon after it was formed and prior to it being present in the mixture at a sufficient concentration for it to precipitate. Thus, when using methods of the invention, it was possible to be quite accurate when choosing the stoichiometric amount of D since the amount of in situ Schwartz Reagent generated from known amounts of A and B was predictable. This predictability is in contrast to previous methods of using Schwartz Reagent that were complicated in this regard by Schwartz Reagent's susceptibility to degradation and limited solubility in most solvents.

Embodiments of the invention comprise mixtures in solution. Any solvent that does not inhibit the method would be suitable. In studies described herein, such suitable solvents included tetrahydrofuran (THF), 1,2-dimethoxyethane (DME), dioxane, 2-MeTHF, diethyl ether, methylene chloride ($CH_2Cl_2$), chloroform ($CHCl_3$), toluene, and combinations thereof.

The in situ method described herein may be suitable for any reaction where Schwartz Reagent has been used in previous methods. Although extensive studies of the in situ method are described herein for many different aryl tertiary amide (see entries 12 and 34 of Table 1 as well as benzamides in entries 1-11, 18-32, and 34 of Table 1) and aryl O-carbamate substrates (see Table 2), representative examples of other types of compounds have also been studied to demonstrate the breadth of this method. Such representative examples include aliphatic tertiary amides (see entries 13-17 of Table 1), an aliphatic tertiary amide with no aryl moieties (see entry 13 of Table 1), and aryl N-carbamates (see Table 3).

Results of the extensive studies that were conducted using the in situ method to reductively cleave tertiary benzamides, aryl O-carbamates are summarized in Tables 1 and 2. Reaction times were short and yields were high. An advantage of the short reaction times of the in situ method is that there is less time for side reactions to occur. The fast reaction times are likely due, at least in part, to the in situ method solving the problem of the Schwartz Reagent's poor solubility, as indicated by the lack of formation of precipitates during the reactions of A, B and D in various solvents. This improvement in solubility may also account for the increased yields that were seen for the in situ method when compared to the Georg method. Table 4 allows for a convenient comparison of experimental parameters for the in situ method and the Georg method. It is noted that for in situ reactions with tertiary amide substrates no precipitate of Schwartz Reagent intermediate was visible in the reaction vessel. However, for reactions with certain O-carbamates, which have longer reaction times and are conducted at lower temperatures, precipitate was observed. Studies were also conducted to probe the effect of solvent and reductant for a selected tertiary benzamide. The tertiary benzamide that was selected was 4-bromo tertiary benzamide (see scheme at top of Table 5 for structural information).

By keeping the solvent choice constant and varying the reductant, the effect of reductant on reaction times and yields was determined. Similarly, by keeping the reductant choice constant and varying the solvent, the effect of solvent on reaction times and yields was determined. Results of both of these studies appear in Table 5. Interestingly, both solvent and reductant affected reaction times and isolated yields. For example, a dramatic solvent effect was noted for diethyl ether relative to THF. The reaction time was reduced from eight min. to two min. and the yield increased from 75% to 96%. For comparison purposes, solvent effects on the Georg method are shown in Table 6 for another tertiary benzamide.

Although the substrates in Table 5 (in situ method) and Table 6 (Georg method) differ in the nature of a ring substituent, their results allow a comparison of the dramatically different results obtained using the currently described in situ method versus those of the Georg method. For example, in dioxane, the in situ method yield was 96%, which was obtained in 8 min. of reaction time, compared to 15% in 30 min. for the Georg method. Similarly in toluene, the in situ method yield was 94% in 2 minutes, compared to 15% in 30 min. for the Georg method. Most notably, in chloroform ($CHCl_3$), the in situ method yield was 80% in 8 min., compared to 0% after 30 min. for the Georg method (see Spletstoser, J. T.; White, J. M.; Tunoori, A. R.; Georg, G. I. *J. Am. Chem. Soc.* 2007, 129, 3408-3419).

As shown in Tables 2 and 3, appropriate relative amounts of the aryl O-carbamate and N-heteroaryl N-carbamate substrates are stoichiometrically higher than for tertiary amide substrates. For a mixture of A, B and aryl O-carbamate, a ratio of 3:3:1 was effective (see Tables 2 and 4). For a mixture of A, B and N-heteroaryl N-carbamate, a ratio of 3:3:1 was effective (see Table 3). A higher relative amount of Schwartz Reagent versus O-carbamate was also required in the Georg method. Notably, the relative amounts of A, B and D that are recommended for the in situ method when D is a tertiary amide were determined to be 1.4 equivalents: 1.4 equivalents: 1 (see Table 1). This is a lesser ratio than that required for the Georg method (1.5 to 2 equivalents) for the same conversion reactions. The decrease in number of equivalents required may be explained by the elimination of solubility problems by removing the need for pre-prepared Schwartz Reagent.

This in situ method has practical and general value. Investigations have been conducted that experimentally confirmed the viability of the in situ method for reductions of aromatic and heteroaromatic tertiary amides to their corresponding benzaldehydes. Investigations have also been conducted that confirmed that the in situ method it is effective for the reduction of aryl O-carbamates to their corresponding phenols. Results of the investigations with substrates such as tertiary benzamides and aryl O-carbamates are further described in the Working Examples, Figures and Tables.

Referring to Table 1, experimental parameters are shown for reductive cleavage reactions using the in situ method of various tertiary benzamides to form benzaldehydes. These reactions were conducted as described in Example 1, with $LiAlH(OBu-t)_3$ and $Cp_2ZrCl_2$ at stated ratios in THF at RT. Yields, reaction times, and the number of equivalents of $Cp_2ZrCl_2$ and $LiAlH(OBu-t)_3$ relative to substrate are reported.

Referring to Table 2, experimental parameters are shown for reductive cleavage reactions using the in situ method of various aryl O-carbamates to form aromatic alcohols. These reactions were conducted as described in Example 2, with $LiAlH(OBu-t)_3$ and $Cp_2ZrCl_2$ at stated ratios in THF at 0° C. to RT. For ease of comparison, yields for reductive cleavage reactions using the Georg method are reported in the rightmost column of Table 2 (see Morin, J., M. Sc. Thesis, Queen's University at Kingston, 2007).

Referring to Table 3, experimental parameters are shown for reductive cleavage reactions using the in situ method of two N-heteroaryl N-carbamates to form indole, with $LiAlH(OBu-f)_3$ and $Cp_2ZrCl_2$ at stated ratios in THF at 0° C. to RT.

Referring to Table 4, select entries from Tables 1 and 2 have been repeated here for ease of comparison of the in situ method versus the Georg method in regard to yields and reaction times.

Referring to Table 5, results of studies are shown wherein solvent or reductant was varied for reductive cleavage using the in situ method of 4-bromotertiary benzamide to form 4-bromobenzaldehyde. Yields and reaction times for these studies are reported.

Referring to Table 6, results of studies are shown wherein solvent was varied for reductive cleavage using the Georg method of N,N-diethyl 4-methoxybenzamide to form 4-methoxybenzaldehyde (see Spletstoser, J. T.; White, J. M.; Tunoori, A. R.; Georg, G. I. *J. Am. Chem. Soc.* 2007, 129, 3408-3419).

Referring to Table 7, results are shown of reactions that were performed that were regio- and stereo-selective conversions (via hydrozirconation and iodination) of three different types of alkynes to their corresponding iodoalkenes using the in situ method, as described in Example 5.

Referring to Table 8, results are shown of performed hydrozirconation—Negishi cross-coupling tandem processes using the in situ method, as described in Example 6.

Aspects of the invention have potential for wide applications. For example, the inventors reasonably expect that the in situ method can be employed in the different types of reactions discussed below. The in situ method can be applied to any reaction where Schwartz Reagent is used, including areas of zirconium chemistry such as hydrozirconation reactions (Marek, I., *Titanium and Zirconium in Organic Synthesis*, Wiley-VCH: Weinheim, 2002; Huang, Z., Negishi, E.-I., *Org. Lett.* 2006, 8, 3675-3678). Results presented in Tables 7 and 8 indicate that the in situ method described herein performs well in hydrozirconation reactions. Notably, benzamides are key substances for the directed ortho metalation (DoM) reaction, a widely used method in organic synthesis. DoM has been applied in the pharmaceutical industry, in some cases on tonne scale, for syntheses of commercial drugs including antitumor and anti-inflammatory drugs (Snieckus, V., *Chem.*

Rev. 1990, 90, 879-933). Aspects of this invention can expand the utilities of benzamide DoM chemistry in syntheses of complex aromatic, including heteroaromatic, compounds by conversion of amide moieties under mild conditions in the presence of other functionalities. Aspects of this invention can simplify syntheses of widely used substances such as phenols and N-heterocycles that are used as intermediates or final products in, for example, pharmaceutical, agrochemical, and materials industries. Thus, aspects of the invention may provide access to new commodity molecules, that, aside from having intrinsic value, may be useful for conversion to substances that can benefit human health and material resources. For all of the above reactions, the inventors reasonably expect that the in situ method has tremendous potential utility.

Kits of the invention include A, which is $Cp_2ZrCl_2$, B, which is a reducing agent that preferentially reduces $Cp_2ZrCl_2$, for use with substrate(s). Non-limiting examples of B include $LiAlH(OBu-t)_3$, $LiBH(s-Bu)_3$, and combinations thereof. Such kits may optionally also include one or more suitable solvents. Such solvents include, but are not limited to, THF, DME, dioxane, 2-MeTHF, diethyl ether, $CH_2Cl_2$, $CHCl_3$, toluene, or combinations thereof.

Such kits may include instructions for use of A and B with substrate(s). Kit instructions may include one or more of text and/or schematics printed on paper or other material, and/or may be supplied via an electronic-readable medium, such as a floppy disc, CD-ROM, DVD-ROM, Zip disc, videotape, audio tape, etc. Detailed instructions may not be physically associated with the kit; instead, a user may be directed to an internet web site specified by the manufacturer or distributor of the kit, or supplied as mail, including electronic mail.

WORKING EXAMPLES AND TABLES

The following examples and tables further illustrate the present invention and are not intended to be limiting in any respect.

Table 1 shows experimental parameters for reductive cleavage of various tertiary benzamides to benzaldehydes using the in situ method, with $LiAlH(OBu-t)_3$ and $Cp_2ZrCl_2$ at stated ratios in THF at RT.

Table 2 shows experimental parameters for reductive cleavage of various aryl O-carbamates to aromatic alcohols using the in situ method, with $LiAlH(OBu-t)_3$ and $Cp_2ZrCl_2$ at stated ratios in THF at 0° C. to RT, and yields for corresponding Georg reactions for comparison purposes (Morin, J. M. Sc. Thesis, Queen's University at Kingston, 2007).

Table 3 shows experimental parameters for reductive cleavage of heteroaryl N-carbamates using the present in situ method, with $LiAlH(OBu-t)_3$ and $Cp_2ZrCl_2$ at stated ratios in THF at 0° C. to RT.

Table 4 shows a comparison of yields and reaction times for in situ method versus Georg method for certain compounds from Tables 1 and 2.

Table 5 shows effects on yields and reaction times of varying solvent and reductant for reductive cleavage of 4-bromo-tertiary benzamide to 4-bromobenzaldehyde using the in situ method.

Table 6 shows effects of solvent for reduction of N,N-diethyl 4-methoxybenzamide to 4-methoxybenzaldehyde using the Georg method.

Table 7 shows experimental parameters for hydrozirconation and iodination reactions that are regio-selective and stereo-selective conversions of alkynes to iodoalkenes.

Table 8 shows experimental parameters for hydrozirconation—Negishi cross-coupling tandem reactions using the in situ method.

Materials

Many of the chemicals discussed below were purchased from Aldrich Chemical Company, Oakville, Ontario, Canada, which is indicated merely by the term "Aldrich". $Cp_2ZrCl_2$ was purchased from Strem Chemicals, Inc. of Newburyport, Mass., USA. $LiAlH(Ot-Bu)_3$ and $LiBH(s-Bu)_3$ were purchased from Aldrich. Silica gel 60, 230-400 mesh, was obtained from EMD Chemicals, Inc. of Darmstadt, Germany.

Example 1

In Situ Conversion Reactions of Tertiary Amides to Aldehydes

Example 1a provides a representative synthetic example in the synthesis of 4-bromobenzaldehyde via the in situ method reaction since the same reaction conditions were used for several other tertiary amide substrates. Experimental parameters for other tertiary amides including reaction times and yields are provided in Table 1 along with the structures of substrates and products. Note that synthetic procedures in regard to preparing certain substrates are provided in Example 4.

Example 1a

Synthesis of 4-Bromobenzaldehyde Using the In Situ Schwartz Reagent Method

To a solution of N,N-diethyl-4-bromo-benzamide (128 mg, 0.5 mmol) (see structural formula at entry 3 of Table 1) and $Cp_2ZrCl_2$ (207 mg, 0.7 mmol, 1.4 eq.) in THF (3 mL) at RT was rapidly added a 1 M tetrahydrofuran (THF) solution of $LiAlH(Ot-Bu)_3$ (0.7 mL, 0.7 mmol, 1.4 eq.). After addition, thin layer chromatography (TLC) using EtOAc/Hexanes showed the substrate had been consumed completely. The reaction was quenched by distilled $H_2O$ immediately. Dilute acid (0.5 N HCl in distilled water) was added until the pH was less than 5. Then EtOAc was added (3×10 mL) and the mixture was extracted. Combined organic layers were washed with brine, dried over $MgSO_4$ and concentrated via evaporation under reduced pressure. Initial purification of the crude product was performed by passing the solution through a filter of silica gel (silica gel 60, 230-400 mesh). Purity was then checked by TLC. If further purification was needed, it was performed by flash column chromatography (silica gel 60, 230-400 mesh) using EtOAc/hexanes as eluent. 4-Bromobenzaldehyde (89 mg, 96% yield) was obtained as a colorless solid. Its melting point was determined to be 55-56° C. (hexanes).

$^1$H NMR (400 MHz, $CDCl_3$) δ ppm: 9.98 (s, 1H), 7.75 (d, J=8.31 Hz, 2H), 7.69 (d, J=8.37 Hz, 2H).

$^{13}$C NMR (101 MHz, $CDCl_3$) δ ppm: 191.02, 135.05, 132.42, 130.94, 129.76.

The physical and spectral data were consistent with those reported by Lee et al. (see Lee, K.; Maleczka, R. E., *Org. Lett.* 2006, 8, 1887-1888), who reported a melting point of 54-56° C.

Example 1b

Synthesis of Other Aldehydes Using the In Situ Schwartz Reagent Method

Further examples of aldehydes that have been synthesized from their corresponding tertiary amides via the in situ method described herein are depicted in Table 1. Reaction steps were as described in representative Example 1a and reaction conditions such as equivalents, reaction times and yields were as shown in Tablet.

Example 2

In Situ Conversion of Aryl O-Carbamates to Aromatic Alcohols

Example 2a

Synthesis of Naphthalen-2-ol Using In Situ Method

To a solution of naphthalen-2-yl diethylcarbamate (73.0 mg, 0.3 mmol) and $Cp_2ZrCl_2$ (265.8 mg, 0.9 mmol, 3 eq.) in THF (4 mL) at 0° C. was added 1 M THF solution of LiAlH(Ot-Bu)$_3$ (0.9 mL, 0.9 mmol, 3 eq.). After addition, the resultant cloudy mixture was warmed to RT and stirred for 3 hours. The reaction was quenched by $H_2O$. The procedures outlined in Example 1a regarding acidification, extraction, and purification were performed. Naphthalen-2-ol (40.8 mg, 95% yield) was obtained as a colorless solid. Its melting point was determined to be 120-121° C. (EtOAc/hexanes). NMR (400 MHz, CDCl$_3$) δ ppm: 7.77 (m, 2H), 7.69 (d, J=8.23 Hz, 1H), 7.44 (td, J=7.52, 0.99 Hz, 1H), 7.34 (td, J=7.51, 0.98 Hz, 1H), 7.15 (d, J=2.33 Hz, 1H), 7.11 (dd, J=8.80, 2.51 Hz, 1H), 5.06 (brs, 1H). $^{13}$C NMR (101 MHz, CDCl$_3$) δ ppm: 153.26, 134.55, 129.84, 128.93, 127.74, 126.51, 126.34, 123.61, 117.69, 109.48. The physical and spectral data were consistent with those reported by Morley et al. (see Morley, J. A.; Woolsey, N. F., *J. Org. Chem.* 1992, 57, 6487-95), who reported a melting point of 121-123° C.

Example 2b

Synthesis of Other Aromatic Alcohols Using In Situ Method

Further examples of aromatic alcohols that were synthesized from their corresponding aryl O-carbamates via the in situ reaction described herein are depicted in Table 2. Reaction steps were as described in representative Example 2a and reaction conditions such as equivalents, reaction times and yields were as shown in Table 2.

Example 3

In Situ Cleavage of Aromatic Heteroaryl N-Carbamates to N-Heteroaryl Compounds

Example 3a

Synthesis of Indole Using In Situ Method

To a solution of N—CONMe$_2$-indole (56.5 mg, 0.3 mmol) and $Cp_2ZrCl_2$ (265.8 mg, 3 eq.) in THF (3 mL) at 0° C. was added 1 M THF solution of LiAlH(Ot-Bu)$_3$ (0.9 mL, 0.9 mmol, 3 eq., Aldrich). After addition, the resultant cloudy mixture was warmed to RT and stirred for 10 min. The reaction was quenched by $H_2O$. HCl (0.5 N) was added to adjust pH to <5. Then the mixture was extracted with EtOAc (3×10 mL). The combined organic layers were washed with brine, dried over MgSO$_4$ and concentrated via evaporation under reduced pressure. Purification was performed by flash column chromatography (silica gel 60, 230-400 mesh) using EtOAc/hexanes as eluent. Following evaporation under reduced pressure, indole (13.6 mg, 39% yield) was obtained as a light yellow solid. $^1$H NMR (400 MHz, CDCl3) δ ppm: 8.13 (br s, 1H), 7.70 (d, J=7.16 Hz, 1H), 7.42 (d, J=7.39 Hz, 1H), 7.32-7.12 (m, 3H), 6.60 (s, 1H); $^{13}$C NMR (101 MHz, CDCl$_3$) δppm: 135.74, 127.82, 124.06, 121.96, 120.70, 119.79, 110.96, 102.63. Physical and spectral data were consistent with those previously reported (Siu, J.; Baxendale, I. R.; Ley, S. V. *Org. Biomol. Chem.* 2004, 2, 160-167).

Example 4

Synthesis of Certain Substrates

Example 4a

Synthesis of N,N-diethyl-3-phenylpropanamide

To a suspension of 3-phenylpropionic acid (455 mg, 3 mmol, Aldrich), in toluene (2 mL) at RT was slowly added thionyl chloride (0.44 mL, 6 mmol, 2 eq., Aldrich). DMF (2 drops) was added and the solution was stirred at RT for 1 h. The reaction mixture was concentrated under reduced pressure and the residue was dissolved in $CH_2Cl_2$ (5 mL). Diethylamine (0.78 mL, 7.5 mmol, 2.5 eq., Aldrich) was added dropwise to the $CH_2Cl_2$ solution at 0° C. and the reaction mixture was warmed and stirred at RT for 30 min. After evaporation under reduced pressure, the resulting residue was sequentially treated with $H_2O$ (5 mL) and EtOAc (5 mL). The organic and aqueous layers were separated and the aqueous layer was extracted with EtOAc (2×5 mL). The combined organic layers were washed with brine, dried with MgSO$_4$ and concentrated under reduced pressure. Purification of the residue was performed using a short silica gel column (silica gel 60, 230-400 mesh) with EtOAc/hexanes as eluent. N,N-diethyl-3-phenylpropanamide (608 mg, 99% yield) was obtained as a colorless oil. Further purification using flash column chromatography was deemed unnecessary. $^1$H NMR (400 MHz, CDCl$_3$) δ ppm: 7.34-7.14 (m, 5H), 3.38 (q, J=7.09 Hz, 2H), 3.22 (q, J=7.12 Hz, 2H), 2.98 (t, J=7.92 Hz, 2H), 2.59 (t, J=7.90 Hz, 2H), 1.16-1.03 (m, 6H); $^{13}$C NMR (101 MHz, CDCl$_3$) δ ppm: 171.16, 141.51, 128.37, 128.35, 125.97, 41.81, 40.13, 35.01, 31.59, 14.20, 13.01.

Example 4b

Preparation of naphthalen-2-yl-N,N-diethylcarbamate

To a suspension of NaH (60% dispersion in mineral oil, 4.6 g, 0.114 mmol, 1.1 eq., Aldrich) in THF (110 mL) at 0° C. was slowly added a solution of naphthalen-2-ol (15.0 g, 0.104 mol, Aldrich) in THF (100 mL). The resulting Mixture was stirred at 0° C. for 1 h, after which N,N-diethylcarbamoyl chloride (14.5 mL, 0.114 mmol, 1.1 eq., Aldrich) was added. The solution was allowed to stir for 3 h at RT. The reaction mixture was quenched with 10 mL of saturated NH$_4$Cl solution and the mixture was transferred to a separatory funnel. Organic and aqueous layers were separated. The aqueous layer was extracted with EtOAc (3×20 mL). The combined organic layers were washed with brine, dried over Na$_2$SO$_4$, and concentrated under reduced pressure to afford the product. Further purification by recrystallization or flash column chromatography was deemed unnecessary. Naphthalen-2-yl-N,N-diethylcarbamate (19.0 g, 75% yield) was obtained as a pink solid, mp 51-53° C. (hexanes); $^1$H NMR (300 MHz, CDCl$_3$) δ ppm: 1.30 (m, 6H), 3.49 (m, 4H), 7.32 (m, 1H), 7.49 (m, 2H), 7.62 (m, 1H), 7.85 (m, 3H).

Example 4c

Preparation of N,N-diethyl-1H-indole-1-carboxamide

To a suspension of NaH (60% dispersion in mineral oil, 1.2 g, 30 mmol, 1.5 eq., Aldrich) in THF (20 mL) at 0° C. was slowly added a solution of indole (2.4 g, 20 mmol, Aldrich) in THF (20 mL). The resulting mixture was stirred at 0° C. for 20 min, after which N,N-diethylcarbamoyl chloride (2.9 mL, 22 mmol, 1.1 eq., Aldrich) was added. Then, the reaction mixture was stirred at 0° C. for 30 min. $H_2O$ (10 mL) was added to quench the reaction and the mixture was transferred to a separatory funnel. The organic and aqueous layers were separated and the aqueous layer was extracted with EtOAc (3×20 mL). The combined organic layers were washed with brine, dried with $MgSO_4$ and concentrated under reduced pressure. After purification of the residue by a short silica gel column (silica gel 60, 230-400 mesh) with EtOAc/hexanes as eluent, the product N,N-diethyl-1H-indole-1-carboxamide (4.3 g, 99% yield) was obtained as a light yellow oil. Further purification using flash column chromatography was deemed unnecessary. $^1$H NMR (400 MHz, $CDCl_3$) δ ppm: 7.67 (d, J=8.17 Hz, 1H), 7.63 (d, J=7.65 Hz, 1H), 7.36-7.26 (m, 2H), 7.21 (t, J=7.24 Hz, 1H), 6.62 (d, J=2.77 Hz, 1H), 3.51 (q, J=7.10 Hz, 4H), 1.27 (t, J=7.11 Hz, 6H); $^{13}$C NMR (101 MHz, $CDCl_3$) δ ppm: 154.39, 135.51, 129.27, 125.89, 123.36, 121.55, 120.90, 112.98, 105.35, 42.41, 13.46.

Example 5

Regio- and Stereo-Selective Conversion of Alkynes to Iodoalkenes (Via Hydrozirconation) Using the In Situ Method

Example 5a

Synthesis of (E)-1-iodooct-1-ene Using In Situ Method

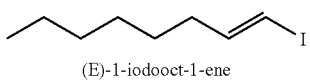

(E)-1-iodooct-1-ene

To a solution of oct-1-yne (113 mg, 1 mmol, available from Lancaster, Pelham, N.H., USA) and $Cp_2ZrCl_2$ (413 mg, 1.4 mmol, 1.4 eq.) in THF (4 mL) at RT was rapidly added a 1 M THF solution of LiAlH(Ot-Bu)$_3$ (1.4 mL, 1.4 mmol, 1.4 eq.). A resulting dark red solution was stirred at RT for 15 min. Then, a solution of iodine (355 mg, 1.4 mmol, 1.4 eq., Aldrich) in THF (2 mL) was added. After additional stirring at RT for 15 min., the reaction mixture was quenched with 1 N HCl, and extracted with diethyl ether (3×10 mL). The organic extracts were combined and washed successively with saturated $Na_2SO_3$, $H_2O$, and brine. The organic residue was then dried over $MgSO_4$ and concentrated via evaporation under reduced pressure. Purification of the residue was performed using a short silica gel column (silica gel 60, 230-400 mesh) with EtOAc/hexanes as eluent. (E)-1-iodooct-1-ene (217 mg, 91% yield) was obtained as a light yellow oil. $^1$H NMR (400 MHz, $CDCl_3$) δ ppm: 6.51 (dt, J=14.30, 7.12 Hz, 1H), 5.97 (d, J=14.31 Hz, 1H), 2.05 (dt, J=7.01, 6.96 Hz, 2H), 1.45-1.34 (m, 2H), 1.33-1.18 (m, 6H), 0.88 (t, J=6.66 Hz, 3H); $^{13}$C NMR (101 MHz, $CDCl_3$) δ ppm: 146.78, 74.21, 36.03, 31.56, 28.58, 28.32, 22.54, 14.04. The physical and spectral data are consistent with those previously reported (see Ren, H.; Krasovskiy, A.; Knochel, P. *Org. Lett.* 2004, 6, 4215-4217).

Example 5b

Synthesis of Other Iodoalkenes Using In Situ Method

Further examples of iodoalkenes that were synthesized from their corresponding alkynes via the in situ reaction described herein are depicted in Table 7. Reaction steps were as described in representative Example 5a and reaction conditions such as equivalents, reaction times and yields were as shown in Table 7.

Example 6

Hydrozirconation—Negishi Cross-Coupling Tandem Process Via In Situ Method

Example 6a

Synthesis of (E)-1-methoxy-4-(oct-1-enyl)benzene from Alkyne (Via Hydrozirconation Using In Situ Method)

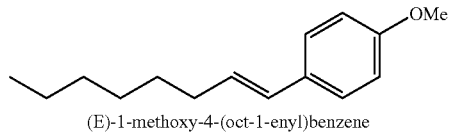

(E)-1-methoxy-4-(oct-1-enyl)benzene

To a solution of oct-1-yne (56.2 mg, 0.5 mmol) and $Cp_2ZrCl_2$ (206.7 mg, 1.4 mmol, 1.4 eq.) in THF (2.5 mL) at RT was rapidly added a 1 M THF solution of LiAlH(Ot-Bu)$_3$ (0.7 mL, 1.4 mmol, 1.4 eq.). A resulting dark red solution was stirred at RT for 15 min. At that time, dry $ZnBr_2$ (157.7 mg, 1.4 mmol, 1.4 eq., Aldrich) and THF (1 mL) were added at RT. After 30 min., 1-iodo-4-methoxybenzene (165.5 mg, 1.4 mmol, 1.4 eq., Aldrich), $Pd(PPh_3)_4$ (11.6 mg, 0.001 mmol, 0.02 eq.) and DMF (1 mL) were added. The resultant mixture was stirred at RT for 5 h and then quenched with 1 N HCl, and extracted with EtOAc (4×5 mL). Organic extracts were combined and washed with $H_2O$ and brine, dried over $MgSO_4$ and concentrated via evaporation under reduced pressure. Purification of the residue was performed using a silica gel column (silica gel 60, 230-400 mesh) with $CH_2Cl_2$/hexanes as eluent. (E)-1-iodooct-1-ene (41.3 mg, 38% yield) was obtained as a colorless oil. $^1$H NMR (400 MHz, $CDCl_3$) δ ppm: 7.27 (d, J=8.62 Hz, 21-1), 6.83 (d, J=8.64 Hz, 2H), 6.31 (d, J=15.79 Hz, 1H), 6.08 (dt, J=14.23, 6.89 Hz, 1H), 3.79 (s, 3H), 2.17 (td, J=7.14, 7.07 Hz, 2H), 1.50-1.40 (m, 2H), 1.38-1.27 (m, 6H), 0.89 (t, J=6.31 Hz, 3H) $^{13}$C NMR (101 MHz, $CDCl_3$) δ ppm: 158.59, 130.84, 129.09, 128.99, 126.93 (2C), 113.89 (2C), 55.27, 33.02, 31.77, 29.50, 28.91, 22.63, 14.09. Physical and spectral data were consistent with those previously reported (see Nakao, Y.; Imanaka, H.; Sahoo, A. K.; Yada, A.; Hiyama, T. *J. Am. Chem. Soc.* 2005, 127, 6952-6953.)

Example 6b

Synthesis of (E)-1-methoxy-4-styrylbenzene Using Hydrozirconation—Negishi Cross-Coupling Tandem Process Via In Situ Method A further example of a hydrozirconation—Negishi cross-coupling tandem process performed via in situ method is depicted in entry 2 of Table 8. Reaction steps were as described in representative Example 6a and reaction conditions such as equivalents, reaction times and yields were as shown in Table 8.

It will be understood by those skilled in the art that this description is made with reference to certain preferred embodiments and that it is possible to make other embodiments employing the principles of the invention which fall within its spirit and scope as defined by the claims.

REFERENCES

Anctil, E. J. G.; Snieckus, V., "The directed ortho metalation—cross coupling nexus. Synthetic methodology for the aryl-aryl and aryl-heteroatom-aryl bonds", *Metal-Catalyzed Cross-Coupling Reactions (2nd Edition)* 2004, 2, 761-813.

Buchwald, S. L.; LaMaire, S. J.; Nielsen, R. B.; Watson, B. T.; King, S. M. *Org. Synth.* 1993, 71, 77-82.

Carr, D. B.; Schwartz, J. *J. Am. Chem. Soc.* 1979, 101, 3521-3531.

Ganem, B.; Franke, R. R. *J. Org. Chem.* 2007, 72, 3981-3987.

Hartung, C. G.; Snieckus, V. *Modern Arene Chemistry* 2002, 330-367.

Huang, Z.; Negishi, "A convenient and genuine equivalent to HZrCp$_2$Cl generated in situ from ZrCp$_2$Cl$_2$DIBAL-H", *Org. Lett.* 2006, 8, 3675-3678.

IUPAC Compendium of Chemical Terminology. 2$^{nd}$ ed. 1997, by Alan D. McNaught and Andrew Wilkinson, Royal Society of Chemistry, Cambridge, UK.

Lee, K.; Maleczka, R. E., "Pd(0)-Catalyzed PMHS reductions of aromatic acid chlorides to aldehydes", Jr. *Org. Lett.* 2006, 8, 1887-1888.

Lipshutz, B. H.; Keil, R,; Ellsworth, E. L., "A new method for the in situ generation of Cp$_2$Zr(H)Cl (Schwartz' Reagent) ", *Tetrahedron Lett,* 1990, 31, 7257-60.

Makabe, H.; Negishi, E., "Hydrogen transfer hydrozirconation of alkenes with iBuZrCp$_2$Cl catalyzed by Lewis-acidic metal compounds containing Al, Zn, Si, Ag, and Pd", *Eur. J. Org. Chem.* 1999, 969-971.

Marek, I., *Titanium and Zirconium in Organic Synthesis*; Wiley-VCH: Weinheim, 2002.

Morin, J.-A., "The regioselective synthesis of highly functionalized naphthalenes and beta-naphthols using directed ortho metalation (DoM) and a new protocol for the reduction of tertiary aryl-O-carbamates by Schwartz Reagent", M. Sc. Thesis, Queen's University at Kingston, 2007.

Morley, J. A.; Woolsey, N. F., "Metal arene complexes in organic synthesis. Hydroxylation, trimethylsilylation and carbethoxylation of some polycyclic aromatic hydrocarbons utilizing $\eta^6$-arene-chromium tricarbonyl complexes", *J. Org. Chem.* 1992, 57, 6487-95.

Murray, C. K.; Zheng, Q. Y.; Cheng, X.; Peterson, S. K., "Preparation of taxol and decetaxel through primary amines", In U.S. Pat. No. 5,679,807,1997.

Schedler, D. J. A.; Li, J.; Ganem, B. *J. Org. Chem.* 1996, 61, 4115-4119.

Schedler, D. J. A.; Godfrey, A. G.; Ganem, B. *Tetrahedron Lett.* 1993, 34, 5035-5038.

Siu, J.; Baxendale, I. R.; Ley, S. V. *Org. Biomol. Chem.* 2004, 2, 160-167.

Snieckus, V. *NATO ASI Ser., Ser. E* 1996, 320, 191-221.

Snieckus, V., "Directed ortho metalation. Tertiary amide and O-carbamate directors in synthetic strategies for polysubstituted aromatics", *Chem. Rev.* 1990, 90, 879-933.

Spletstoser, J. T.; White, J. M.; Tunoori, A. R.; Georg, G. I., "Mild and selective hydrozirconation of amides to aldehydes using Cp$_2$Zr(H)Cl: scope and mechanistic insight", *J. Am. Chem. Soc.* 2007, 129, 3408-3419.

Spletstoser, J. T.; White, J. M.; Georg, G. I., "One-step facile synthesis of deuterium labeled aldehydes from tertiary amides using Cp$_2$Zr(D)Cl", *Tetrahedron Lett.* 2004, 45, 2787-2789.

Wailes, P. C.; Weigold, H. *J. Organomet. Chem.* 1970, 24, 405-411.

White, J. M.; Tunoori, A. R.; Georg, G. I., "Selective reduction with Cp$_2$ZrHCl", *Chemical Innovation* 2000, 30, 23-28.

White, J. M.; Tunoori, A. R.; Georg, G. I., "A novel and expeditious reaction of tertiary amides to aldehydes using Cp$_2$Zr(H)Cl", *J. Am. Chem. Soc.* 2000, 122, 11995-11996.

Wipf, P.; Jahn, H., "Synthetic applications of organochlorozirconocene complexes", *Tetrahedron* 1996, 52, 12853-12910.

Wipf, P.; Kendall, C., "Hydrozirconation and its applications", *Topics in Organometallic Chemistry* 2005, 8, 1-25.

TABLE 1

Experimental parameters for exemplary in situ tertiary amide to aldehyde reductions substrate $\xrightarrow[\text{2. LiAlH(OBu-t)}_3\text{, THF, RT}]{\text{1. Cp}_2\text{ZrCl}_2\text{, THF, RT}}$ product

| Entry | Substrate | Equivalents of Cp$_2$ZrCl$_2$ & LiAlH(OBu-t)$_3$ relative to substrate | Reaction Time (min) | Product | Isolated Yield (%) |
|---|---|---|---|---|---|
| 1 | *2-methylbenzoyl morpholine* | 1.4 | 2 | *2-methylbenzaldehyde (CHO)* | 95 |

TABLE 1-continued

Experimental parameters for exemplary in situ tertiary amide to aldehyde reductions $$\text{substrate} \xrightarrow[\text{2. LiAlH(OBu-t)}_3\text{, THF, RT}]{\text{1. Cp}_2\text{ZrCl}_2\text{, THF, RT}} \text{product}$$

| Entry | Substrate | Equivalents of Cp₂ZrCl₂ & LiAlH(OBu-t)₃ relative to substrate | Reaction Time (min) | Product | Isolated Yield (%) |
|---|---|---|---|---|---|
| 2 | 3-CN-C₆H₄-CONEt₂ | 1.4 | 10 | 3-CN-C₆H₄-CHO | 94 |
| 3 | 4-Br-C₆H₄-CONEt₂ | 1.4 | 2 | 4-Br-C₆H₄-CHO | 96 |
| 4 | 3-(allyloxy)-C₆H₄-CONEt₂ | 1.4 | 2 | 3-(allyloxy)-C₆H₄-CHO | 91 |
| 5 | 3-(OCONEt₂)-C₆H₄-CONEt₂ | 1.4 | 2 | 3-(OCONEt₂)-C₆H₄-CHO | 93 |
| 6 | 3-(OSiEt₃)-C₆H₄-CONEt₂ | 1.4 | 10 | 3-(OSiEt₃)-C₆H₄-CHO | 91 |
| 7 | 4-MeO-3-NO₂-C₆H₃-CONEt₂ | 1.4 | 20 | 4-MeO-3-NO₂-C₆H₃-CHO | 83 |
| 8 | 2-Cl-5-NHBoc-C₆H₃-CONEt₂ | 2.0 | 30 | 2-Cl-5-NHBoc-C₆H₃-CHO | 77 |
| 9 | 2-I-4-MeO-C₆H₃-CONMe₂ | 1.4 | 8 | 2-I-4-MeO-C₆H₃-CHO | 89 |

TABLE 1-continued

Experimental parameters for exemplary in situ tertiary amide to aldehyde reductions $$\text{substrate} \xrightarrow[\text{2. LiAlH(OBu-t)}_3\text{, THF, RT}]{\text{1. Cp}_2\text{ZrCl}_2\text{, THF, RT}} \text{product}$$

| Entry | Substrate | Equivalents of Cp$_2$ZrCl$_2$ & LiAlH(OBu-t)$_3$ relative to substrate | Reaction Time (min) | Product | Isolated Yield (%) |
|---|---|---|---|---|---|
| 10 | 2-chloro-3,4-dimethoxy-N,N-diethylbenzamide | 1.5 | 20 | 2-chloro-3,4-dimethoxybenzaldehyde | 97 |
| 11 | 2-iodo-3-methoxy-5-(tert-butyldimethylsilyloxy)-N,N-diethylbenzamide | 1.8 | 20 | 2-iodo-3-methoxy-5-(tert-butyldimethylsilyloxy)benzaldehyde | 97 |
| 12 | 5-(tert-butoxycarbonyl)-3-(4-(N-Boc-indol-4-yl))-2-(N,N-diethylcarbamoyl)pyridine | 1.8 | 30 | 5-(tert-butoxycarbonyl)-3-(4-(N-Boc-indol-4-yl))pyridine-2-carbaldehyde | 67 |
| 13 | CH$_3$—(CH$_2$)$_8$—CONEt$_2$ | 1.4 | 2 | CH$_3$—(CH$_2$)$_8$—CHO | 87 |
| 14 | 4-(4-chlorophenyl)cyclohexane-1-carboxylic acid diethylamide | 2.0 | 30 | 4-(4-chlorophenyl)cyclohexane-1-carbaldehyde | 83 |
| 15 | 3-phenyl-N,N-diethylpropanamide | 1.4 | 2 | 3-phenylpropanal | 86 |
| 16 | 2-phenoxy-N,N-diethylacetamide | 1.4 | 2 | 2-phenoxyacetaldehyde | 91 |
| 17 | 2-(2-methoxyphenyl)-N,N-diethylacetamide | 1.4 | 2 | 2-(2-methoxyphenyl)acetaldehyde | 87 |
| 18 | 4-(hydroxymethyl)-N,N-diethylbenzamide | 1.4 | 2 | 4-(hydroxymethyl)benzaldehyde | 93[b] |

TABLE 1-continued

Experimental parameters for exemplary in situ tertiary amide to aldehyde reductions $$\text{substrate} \xrightarrow[\text{2. LiAlH(OBu-t)}_3\text{, THF, RT}]{\text{1. Cp}_2\text{ZrCl}_2\text{, THF, RT}} \text{product}$$

| Entry | Substrate | Equivalents of Cp$_2$ZrCl$_2$ & LiAlH(OBu-t)$_3$ relative to substrate | Reaction Time (min) | Product | Isolated Yield (%) |
|---|---|---|---|---|---|
| 19 | 4-(MeO$_2$C)-C$_6$H$_4$-CONEt$_2$ | 1.6 | 2 | 4-(MeO$_2$C)-C$_6$H$_4$-CHO | 90 |
| 20 | 3-(NMe$_2$)-C$_6$H$_4$-CONEt$_2$ | 1.4 | 2 | 3-(NMe$_2$)-C$_6$H$_4$-CHO | 81 |
| 21 | 3-(NHCbz)-C$_6$H$_4$-CONEt$_2$ | 2.0 | 2 | 3-(NHCbz)-C$_6$H$_4$-CHO | 99 |
| 22 | 2-(OMe)-C$_6$H$_4$-CONR$^1$R$^2$, R$^1$, R$^2$ = Me, Me | 1.4 | 2 | 2-(OMe)-C$_6$H$_4$-CHO | 94 |
| 23 | 2-(OMe)-C$_6$H$_4$-CON(Et)$_2$ | 1.4 | 2 | 2-(OMe)-C$_6$H$_4$-CHO | 93 |
| 24 | 4-[(Et$_2$N)$_2$P(O)O]-C$_6$H$_4$-CONEt$_2$ | 1.4 | 2 | 4-[(Et$_2$N)$_2$P(O)O]-C$_6$H$_4$-CHO | 91 |
| 25 | 4-(TfO)-C$_6$H$_4$-CONEt$_2$ | 1.4 | 2 | 4-(TfO)-C$_6$H$_4$-CHO | 95 |
| 26 | 2-(PPh$_2$)-C$_6$H$_4$-CONEt$_2$ | 1.8 | 2 | 2-(PPh$_2$)-C$_6$H$_4$-CHO | 93 |
| 27 | 4-[(t-Bu)S(O)]-C$_6$H$_4$-CONEt$_2$ | 1.4 | 2 | 4-[(t-Bu)S(O)]-C$_6$H$_4$-CHO | 95 |

TABLE 1-continued

Experimental parameters for exemplary in situ tertiary amide to aldehyde reductions substrate $\xrightarrow[\text{2. LiAlH(OBu-t)}_3\text{, THF, RT}]{\text{1. Cp}_2\text{ZrCl}_2\text{, THF, RT}}$ product

| Entry | Substrate | Equivalents of Cp$_2$ZrCl$_2$ & LiAlH(OBu-t)$_3$ relative to substrate | Reaction Time (min) | Product | Isolated Yield (%) |
|---|---|---|---|---|---|
| 28 | 2-(PhSO$_2$)C$_6$H$_4$-CONEt$_2$ | 1.4 | 2 | 2-(PhSO$_2$)C$_6$H$_4$-CHO | 92 |
| 29 | 4-Br-C$_6$H$_4$-CON(i-Pr)$_2$ | 2.2 | 25 | 4-Br-C$_6$H$_4$-CHO | 88 |
| 30 | 2-I-C$_6$H$_4$-C(O)N(Me)Ph | 1.4 | 7 | 2-I-C$_6$H$_4$-CHO | 90 |
| 31 | 2-(TMSCH$_2$)-3-Cl-C$_6$H$_3$-CONEt$_2$ | 1.4 | 2 | 2-(TMSCH$_2$)-3-Cl-C$_6$H$_3$-CHO | 87 |
| 32 | 3-MeO-5-HO-C$_6$H$_3$-CONEt$_2$ | 1.4 | 2 | 3-MeO-5-HO-C$_6$H$_3$-CHO | 80[b] |
| 33 | 4-Me-2-TMS-furan-3-CONEt$_2$ | 1.4 | 20 | 4-Me-2-TMS-furan-3-CHO | 77 |
| 34 | 1-(3-MeO-C$_6$H$_4$)-naphthalen-2-yl-CONEt$_2$ | 1.4 | 2 | 1-(3-MeO-C$_6$H$_4$)-naphthalen-2-yl-CHO | 90 |

TABLE 1-continued

Experimental parameters for exemplary in situ tertiary amide to aldehyde reductions $$\text{substrate} \xrightarrow[\text{2. LiAlH(OBu-t)}_3\text{, THF, RT}]{\text{1. Cp}_2\text{ZrCl}_2\text{, THF, RT}} \text{product}$$

| Entry | Substrate | Equivalents of Cp$_2$ZrCl$_2$ & LiAlH(OBu-t)$_3$ relative to substrate | Reaction Time (min) | Product | Isolated Yield (%) |
|---|---|---|---|---|---|
| 35 | 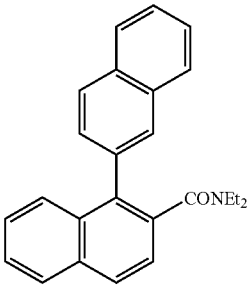 | 1.4 | 2 | 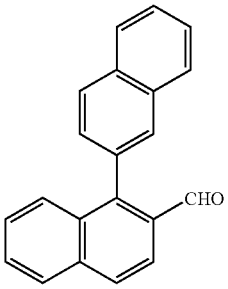 | 89 |

[b]Reductions carried out wherein a solution of Cp$_2$ZrCl$_2$ (1.4 eq.) was added to a solution of substrate and LiAlH(OBu-t)$_3$ (2.4 eq.).

TABLE 2

Reductive cleavage of exemplary aryl O-carbamates to aromatic alcohols using the in situ Schwartz Reagent method $$\text{Ar---OCONEt}_2 \xrightarrow[\begin{array}{c}\text{2. LiAlH(OBu-t)}_3\text{, THF, 0 deg. C.-RT}\\\text{3. 0.5 N HCl}\end{array}]{\text{1. Cp}_2\text{ZrCl}_2\text{, THF, 0 deg. C.}} \text{Ar---OH}$$

| Entry | Substrate | Equivalents of Cp$_2$ZrCl$_2$ & LiAlH(Ot-Bu)$_3$ relative to substrate | Reaction Time (min) | Product | Isolated Yield (%) | Yield for corresponding Georg method |
|---|---|---|---|---|---|---|
| 1 | 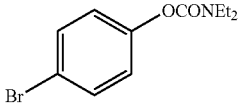 | 3.0 | 3 h | 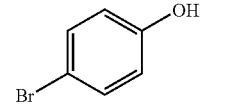 | 96 | 88 |
| 2 | 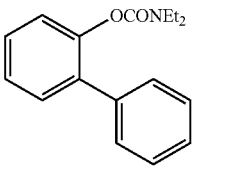 | 3.0 | 3 h | 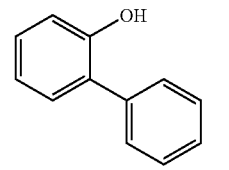 | 89 | 88 |
| 3 | 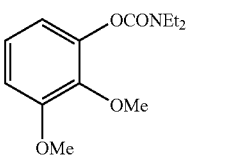 | 3.0 | 3 h | 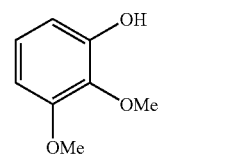 | 90 | 78 |

TABLE 2-continued

Reductive cleavage of exemplary aryl O-carbamates to aromatic alcohols using the in situ Schwartz Reagent method Ar—OCONEt$_2$ $\xrightarrow{\text{1. Cp}_2\text{ZrCl}_2\text{, THF, 0 deg. C.} \atop \text{2. LiAlH(OBu-t)}_3\text{, THF, 0 deg. C.-RT} \atop \text{3. 0.5 N HCl}}$ Ar—OH

| Entry | Substrate | Equivalents of Cp$_2$ZrCl$_2$ & LiAlH(Ot-Bu)$_3$ relative to substrate | Reaction Time (min) | Product | Isolated Yield (%) | Yield for corresponding Georg method |
|---|---|---|---|---|---|---|
| 4 | 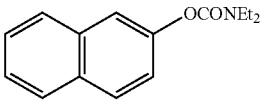 | 3.0 | 3 h | 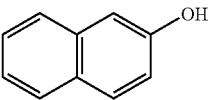 | 95 | 81 |
| 5 | 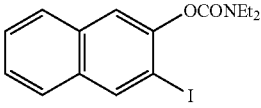 | 3.0 | 5 h | 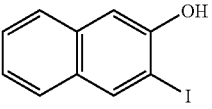 | 81 | |
| 6 | 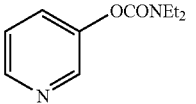 | 3.0 | 3 h | 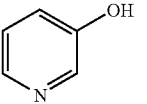 | 90 | 87 |

TABLE 3

Reductive cleavage of exemplary heterocyclic N-carbamates to N-heterocycles using the in situ Schwartz Reagent method

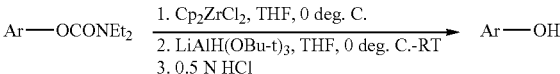

| Entry | Substrate | Equivalent of in situ Schwartz reagent | Time | Product | Isolated Yield (%) |
|---|---|---|---|---|---|
| 1 | 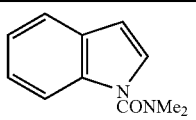 | 3.0 | 10 min | 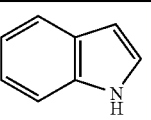 | 39 |
| 2 | 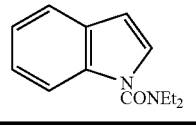 | 3.0 | 10 min | 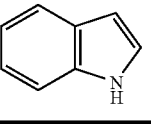 | 42 |

TABLE 4

Comparison of experimental parameters for Georg method vs. in situ method

Georg method

| Substrate | Eq. of Cp$_2$Zr(H)Cl relative to substrate | Rxn time & temp. | Product | Yield (%) |
|---|---|---|---|---|
| 4-Br-C$_6$H$_4$-CONEt$_2$ | 1.5 | 10 min RT | 4-Br-C$_6$H$_4$-CHO | 73 |
| 3-(allyloxy)-C$_6$H$_4$-CONEt$_2$ | 1.5 | 20 min RT | 3-(allyloxy)-C$_6$H$_4$-CHO | 72 |
|  |  |  | 3-(propyloxy)-C$_6$H$_4$-CHO | 7 |
| 2-naphthyl-OCONEt$_2$ | 3 | 18 h RT | 2-naphthol | 81 |

In situ method

| Substrate | Eq. of Cp$_2$ZrCl$_2$ & LiAlH(Ot-Bu)$_3$ relative to substrate | Rxn time & temp. | Product | Yield (%) |
|---|---|---|---|---|
| 4-Br-C$_6$H$_4$-CONEt$_2$ | 1.4 | 2 min. RT | 4-Br-C$_6$H$_4$-CHO | 96 |
| 3-(allyloxy)-C$_6$H$_4$-CONEt$_2$ | 1.4 | 2 min. RT | 3-(allyloxy)-C$_6$H$_4$-CHO | 91 |
| 2-naphthyl-OCONEt$_2$ | 3 | 3 h 0° C.-RT | 2-naphthol | 95 |

TABLE 5

Effects of reaction conditions for in situ reaction of tertiary benzamide to aldehyde

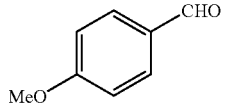

| Equivalent of Reductant | Reductant | Solvent | Reaction Time (min.) | Yield (%) |
|---|---|---|---|---|
| 1.4 | LiAlH(OBu-t)$_3$ | DME | 2 | 97 |
| 1.4 | LiAlH(OBu-t)$_3$ | CH$_2$Cl$_2$ | 2 | 92 |
| 1.4 | LiAlH(OBu-t)$_3$ | 2-MeTHF | 10 | 84[a] |
| 1.4 | LiAlH(OBu-t)$_3$ | dioxane | 8 | 96 |
| 1.4 | LiAlH(OBu-t)$_3$ | diethyl ether | 8 | 75[b,c] |
| 1.4 | LiAlH(OBu-t)$_3$ | CHCl$_3$ | 8 | 80[d] |
| 1.4 | LiAlH(OBu-t)$_3$ | toluene | 2 | 94[b] |
| 1.4 | LiAlH(OBu-t)$_3$ | THF | 2 | 96 |
| 1.4 | LiBH(s-Bu)$_3$ | THF | 2 | 91 |
| 0.35 | LiAlH$_4$ | THF | 2 | 66[e] |
| 1.4 | DIBAL-H | THF | 30 | 50[f] |

Unless stated differently, solution concentrations were 0.1 to 0.3 M of substrate.
[a] Starting material was also isolated (8%).
[b] Carried out at 0.03 M, Cp$_2$ZrCl$_2$ was not completely solubilized until reductant was added.
[c] Starting material was also isolated (18%).
[d] Starting material was also isolated (19%).
[e] By-products benzyl alcohol and benzylamine were also detected by GC-MS in a ratio of 8:1:1 of aldehyde:alcohol:amine.
[f] Starting material was also isolated (38%).

TABLE 6

Comparison of solvents for the reduction of N,N-diethyl 4-methoxybenzamide to 4-methoxybenzaldehyde using the Georg method

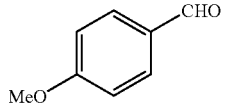

| Entry | Solvent | Time (min) | Yield (%) |
|---|---|---|---|
| 1 | THF | 30 | 99 |
| 2 | oxetane | 30 | 95 |
| 3 | dioxane | 30 | 15 |
| 4 | pyridine | 30 | 15 |
| 5 | CHCl$_3$ | 30 | 0 |
| 6 | toluene | 30 | 15 |

TABLE 7

Regio- and stereo-selective conversion of alkynes to iodoalkenes using in situ method

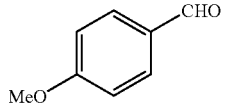

| Entry | Substrate | Product | Isolated Yield (%) |
|---|---|---|---|
| 1 | 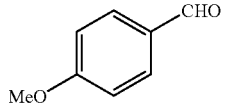 | 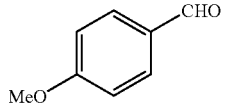 | 91 |
| 2 | 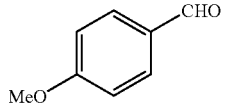 | 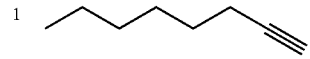 | 91 |
| 3 | 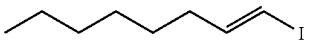 | 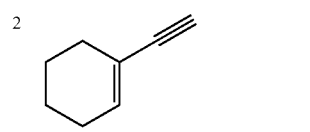 | 94 |

TABLE 8

Hydrozirconation—Negishi cross-coupling tandem process via in situ method

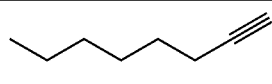

| Entry | Substrate | Product | Isolated Yield (%) |
|---|---|---|---|
| 1 | 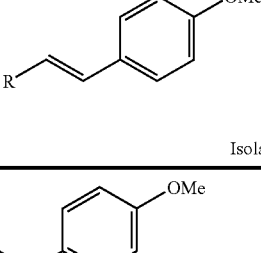 | 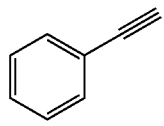 | 38 |
| 2 | 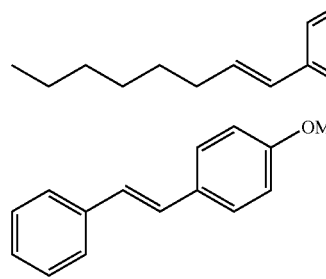 | 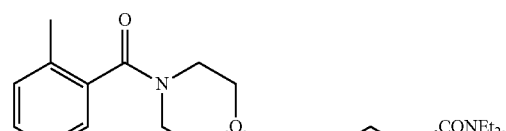 | 32 |

We claim:

1. A method of converting a substrate to a product comprising:
    combining at substantially the same time selected amounts of A, B, and D in a solvent;
    allowing time for reactions to proceed; and
    obtaining product E;
    where:
    A is $Cp_2ZrCl_2$,
    B is a reducing agent that preferentially reacts with A to form an intermediate,
    D is a substrate that is reduced by the intermediate, and
    E is a reduced form of D.

2. The method of claim 1, wherein D is a tertiary amide and E is an aldehyde.

3. The method of claim 1, wherein D is an aryl O-carbamate and E is an aromatic alcohol.

4. The method of claim 1, wherein D is an aromatic N-heteroaryl N-carbamate and E is an N-heteroaryl compound.

5. The method of claim 1, wherein B is $LiAlH(OBu-t)_3$, $LiBH(s-Bu)_3$, or a combination thereof.

6. The method of claim 2, wherein the tertiary amide is an aryl tertiary amide.

7. The method of claim 6, wherein aryl is heteroaryl.

8. The method of claim 2, wherein the combination is at about room temperature.

9. The method of claim 1, wherein the selected amounts of A, B, and D are an excess of A and B over D.

10. A kit for reducing a substrate comprising:
    A and B,
    where A is $Cp_2ZrCl_2$ and B is a reducing agent that selectively reduces A; and
    instructions for reducing the substrate by combining at substantially the same time selected amounts of A, B and the substrate in a solvent.

11. The kit of claim 10, wherein B is $LiAlH(OBu-t)_3$, $LiBH(s-Bu)_3$, or a combination thereof.

12. The method of claim 2, wherein the tertiary amide is an aliphatic tertiary amide.

13. The method of claim 1, wherein D is a substrate selected from:

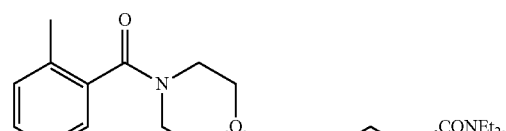

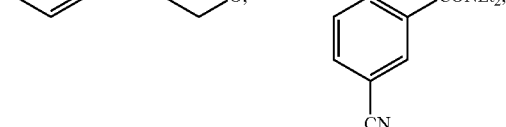

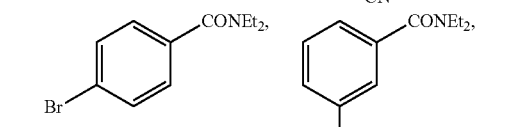

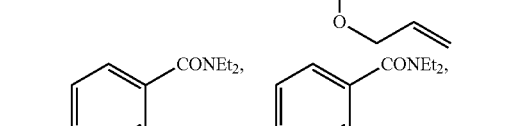

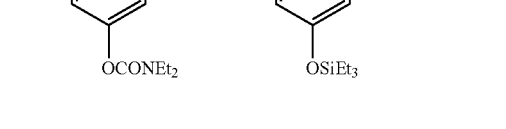

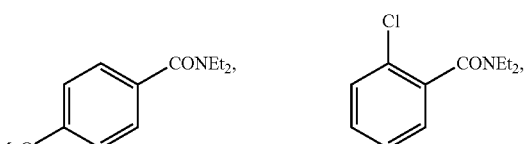

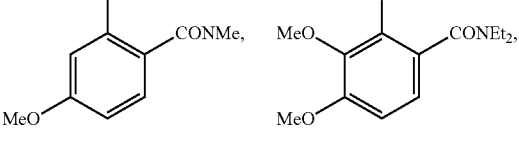

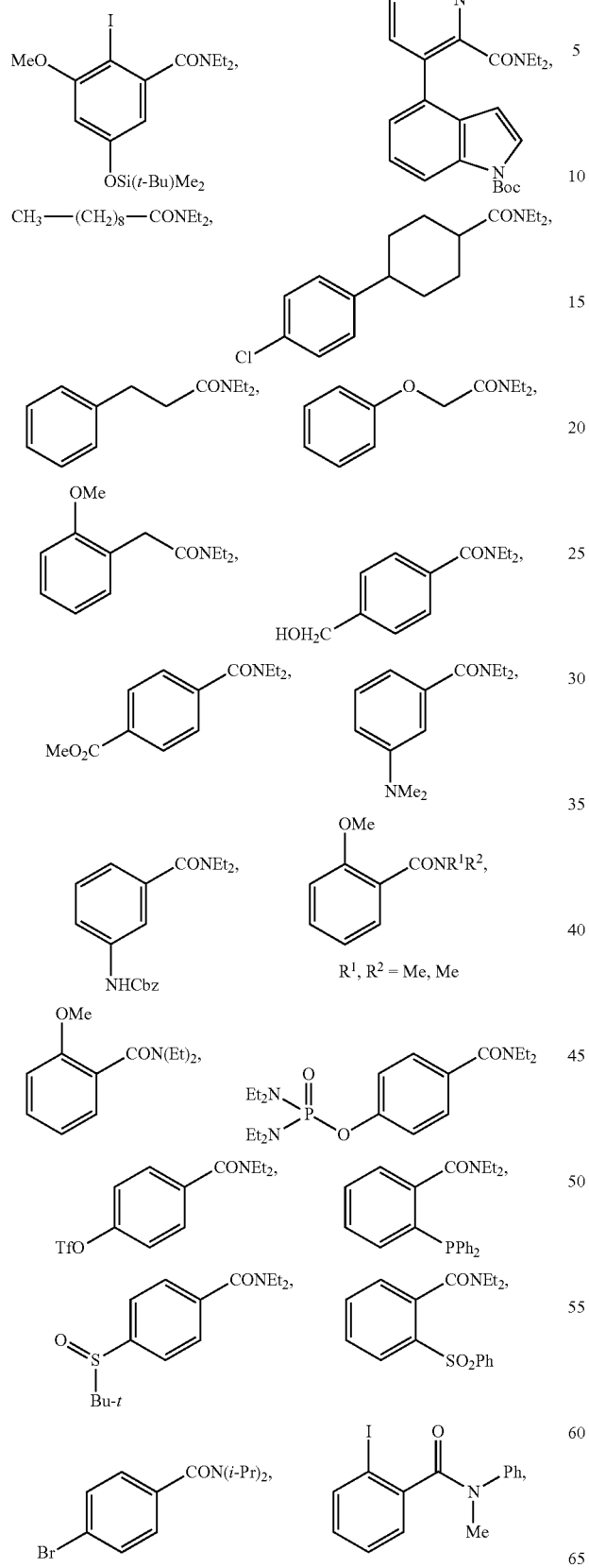
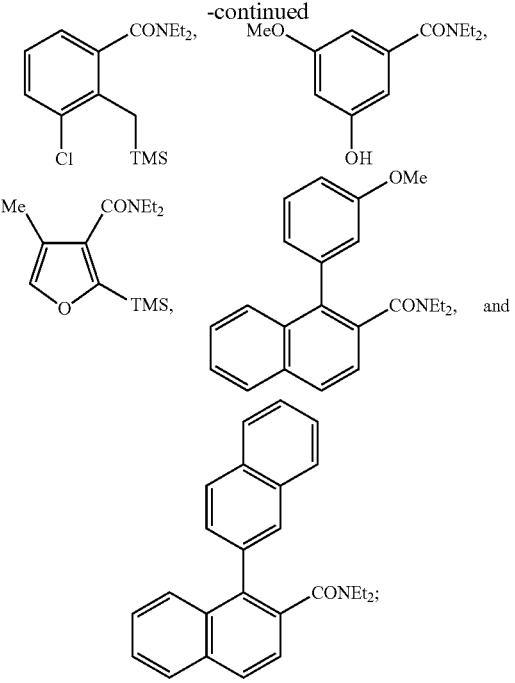
and E is a corresponding product selected from:
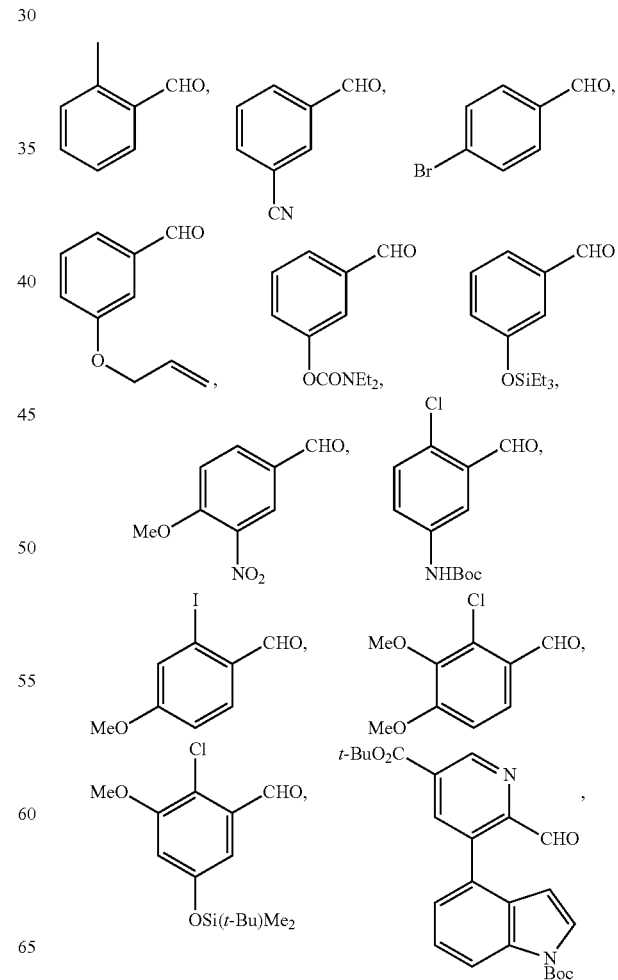

-continued
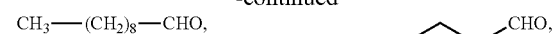
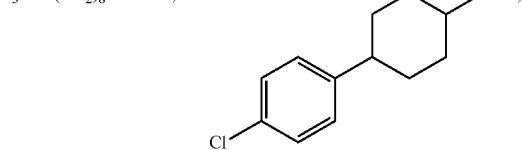
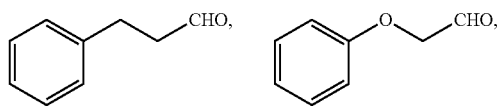
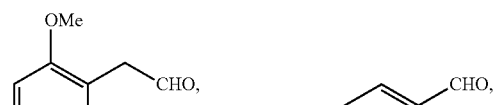
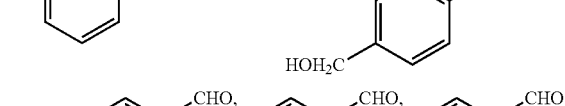
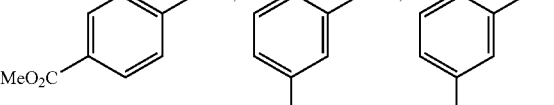
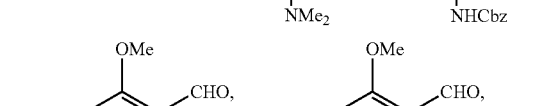
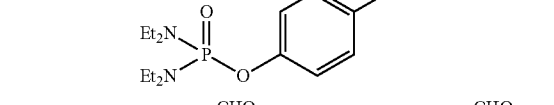
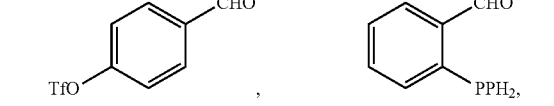
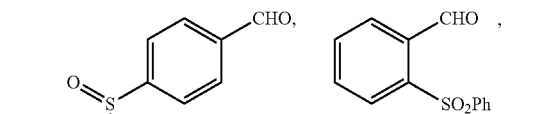
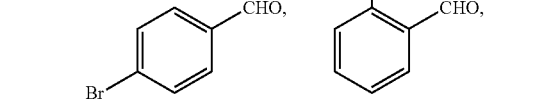
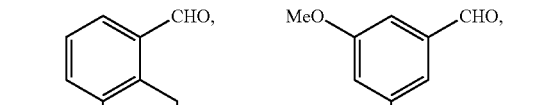
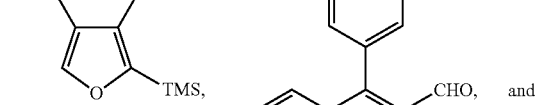
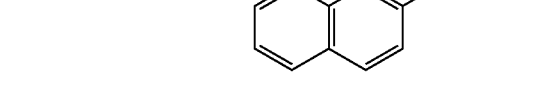
-continued
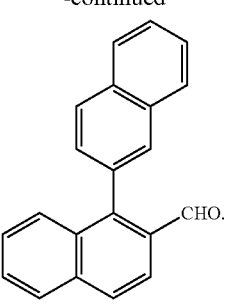
14. The method of claim 1, wherein D is a substrate selected from:
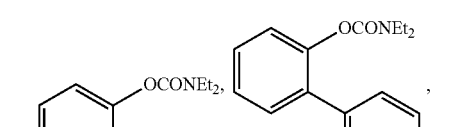
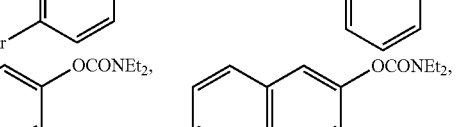
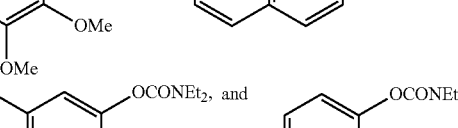
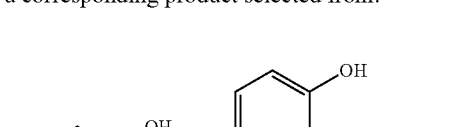
and E is a corresponding product selected from:
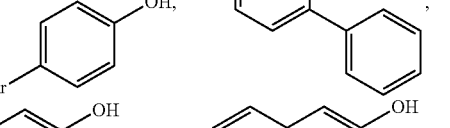
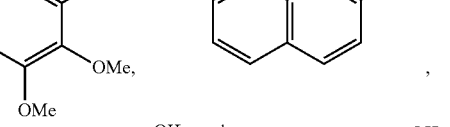
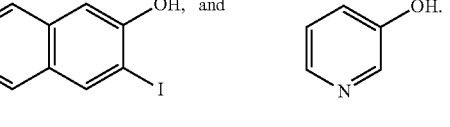
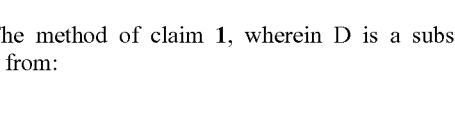
15. The method of claim 1, wherein D is a substrate selected from:
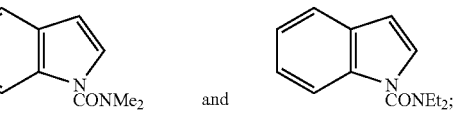

and E is a corresponding product selected from:

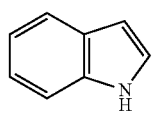 and 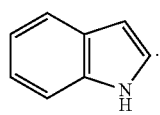.

16. The method of claim 1, wherein D is a substrate selected from:

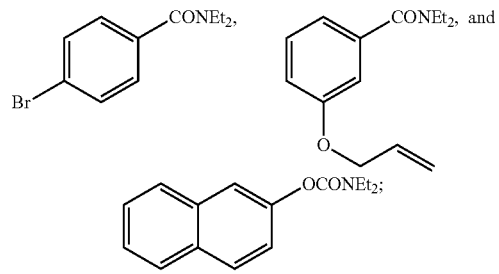

and E is a corresponding in situ method product selected from:

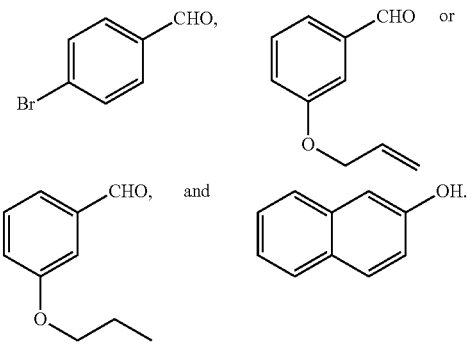

17. The method of claim 1, wherein D is a substrate selected from:

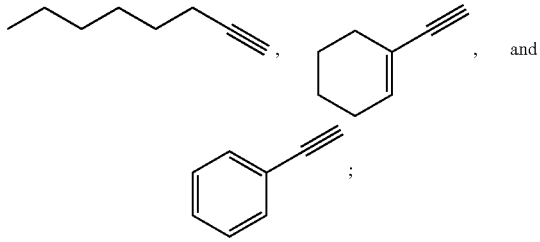

and E is a corresponding product selected from:

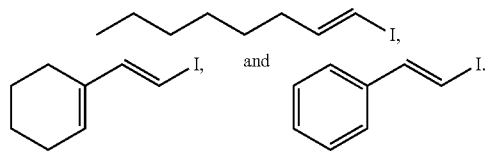

18. The method of claim 1, wherein D is a substrate selected from:

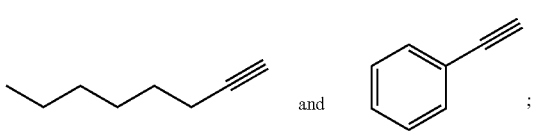

and E is a corresponding product selected from:

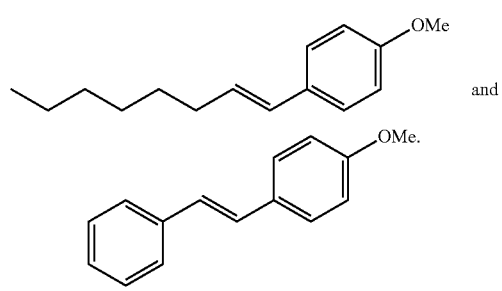

19. A compound which is:

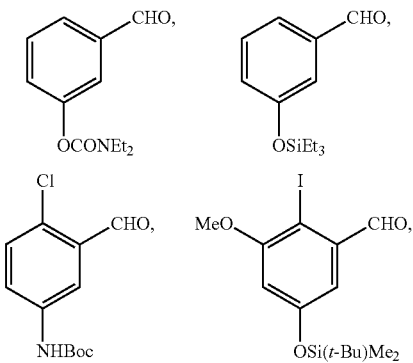

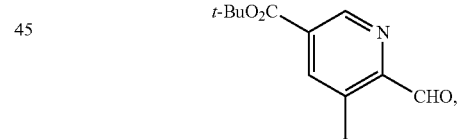

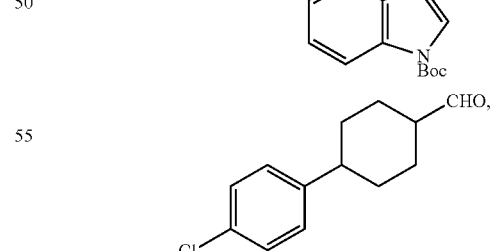

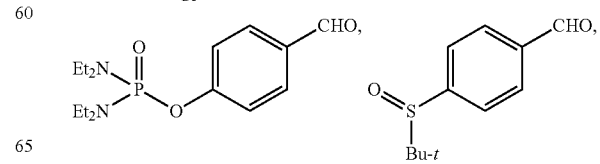

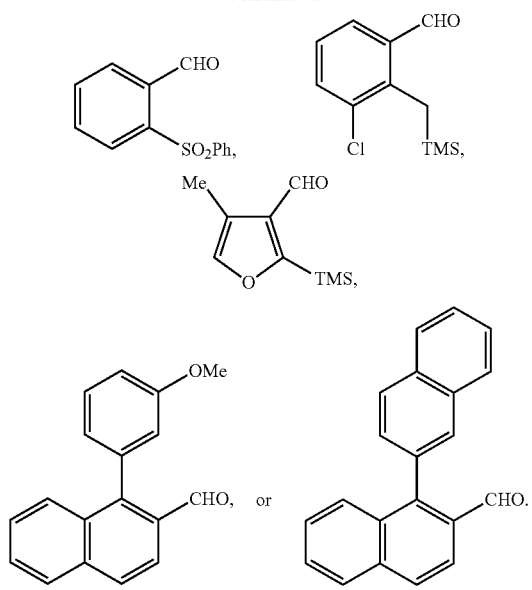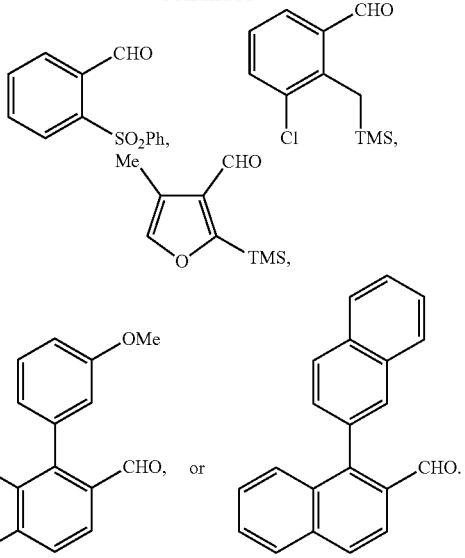

20. A compound E made by the method of claim 1, wherein the compound E is:

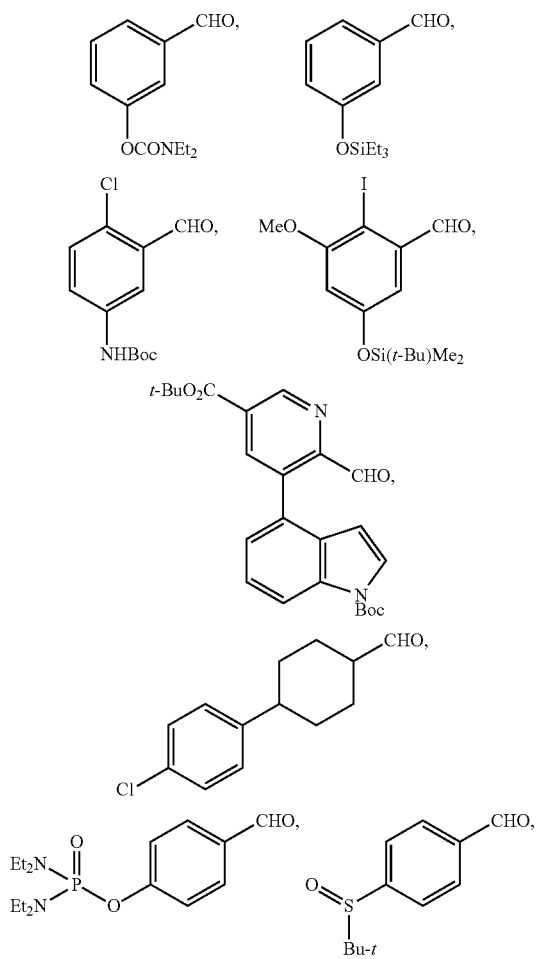

21. The method of claim 1, wherein the combination starts at about 0° C. and is allowed to warm to about room temperature.

22. The method of claim 1, wherein the solvent comprises THF, DME, dioxane, 2-MeTHF, diethyl ether, $CH_2Cl_2$, $CHCl_3$, toluene or a combination thereof.

23. The method of claim 2, wherein the time allowed for reactions to proceed is about two to about ten minutes.

24. The method of claim 2, wherein the selected amounts of A, B and D are in a ratio of 1.4:1.4:1.

25. The method of claim 1, wherein the selected amounts of A, B and D are in a ratio of 1.5:1.5:1, 1.8:1.8:1 or 2:2:1.

26. The method of claim 3, wherein the selected amounts of A, B and D are in a ratio of 3:3:1.

27. The method of claim 4, wherein the selected amounts of A, B and D are in a ratio of 3:3:1.

28. The kit of claim 11, further comprising solvent.

29. The kit of claim 28, wherein the solvent is THF, DME, dioxane, 2-MeTHF, diethyl ether, $CH_2Cl_2$, $CHCl_3$, toluene or a combination thereof.

30. The method of claim 2, wherein the time allowed for reactions to proceed is greater than about two minutes.

31. The method of claim 1, wherein E is a hydrozirconation product of D.

32. The method of claim 1, wherein E is further reacted to form a new product.

33. The method of claim 32, wherein E is further reacted with $X_2$ or $ZnX_2$ where X is a halide.

34. The compound of claim 19 which is:

35. The compound of claim 19 which is
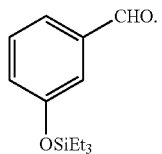
36. The compound of claim 19 which is:
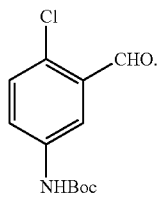
37. The compound of claim 19 which is:
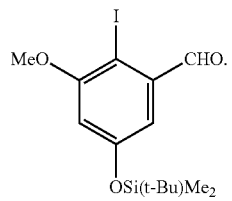
38. The compound of claim 19 which is:
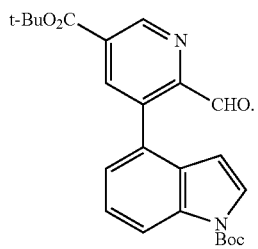
39. The compound of claim 19 which is:
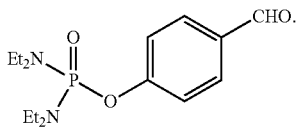
40. The compound of claim 19 which is:
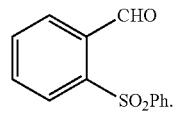
41. The compound of claim 19 which is:
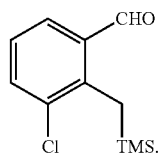
42. The compound of claim 19 which is:
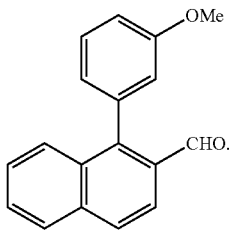
43. The compound of claim 19 which is:
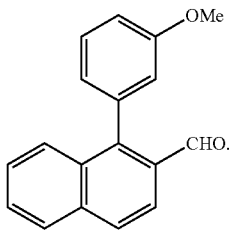
* * * * *

UNITED STATES PATENT AND TRADEMARK OFFICE
CERTIFICATE OF CORRECTION

PATENT NO. : 8,168,833 B2
APPLICATION NO. : 12/630185
DATED : May 1, 2012
INVENTOR(S) : Yigang Zhao and Victor A. Snieckus Page 1 of 1

It is certified that error appears in the above-identified patent and that said Letters Patent is hereby corrected as shown below:

Under Columns 42 and 43, Lines 52-60, 8-12 and 13-24, Claim 19, delete the following compounds:

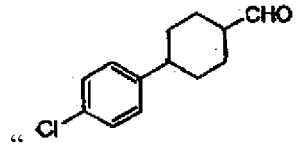 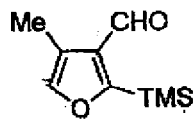 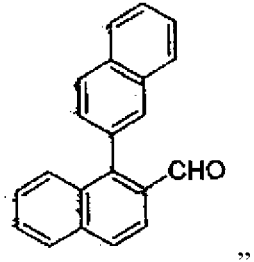

Under Columns 43 and 44, Lines 52-60, 8-12 and 13-24, Claim 20, delete the following compounds:

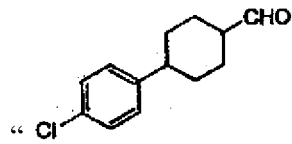 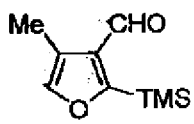 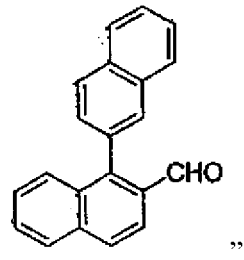

Signed and Sealed this
Tenth Day of July, 2012

David J. Kappos
*Director of the United States Patent and Trademark Office*